(12) United States Patent
Morris

(10) Patent No.: US 6,849,239 B2
(45) Date of Patent: Feb. 1, 2005

(54) METHOD AND APPARATUS FOR ANALYZING MIXTURES OF GASES

(75) Inventor: Patricia A. Morris, Montchanin, DE (US)

(73) Assignee: E. I. du Pont de Nemours and Company, Wilmington, DE (US)

(*) Notice: Subject to any disclaimer, the term of this patent is extended or adjusted under 35 U.S.C. 154(b) by 82 days.

(21) Appl. No.: 10/117,472

(22) Filed: Apr. 5, 2002

(65) Prior Publication Data

US 2004/0013571 A1 Jan. 22, 2004

Related U.S. Application Data

(63) Continuation-in-part of application No. 09/977,791, filed on Oct. 15, 2001.
(60) Provisional application No. 60/240,619, filed on Oct. 16, 2000, and provisional application No. 60/246,946, filed on Nov. 9, 2000.

(51) Int. Cl.$^7$ .......................... G01N 7/00; G01N 21/00; G01N 27/00; G01N 31/00; G01N 33/00
(52) U.S. Cl. .................. 422/98; 422/50; 422/83; 422/88; 422/94; 422/95; 422/96; 422/97; 436/43; 436/149; 73/1.01; 73/1.02; 73/23.2; 73/23.31; 73/31.06
(58) Field of Search .................... 422/50, 83, 88, 422/94, 95, 96, 97, 98; 436/43, 149; 73/1.01, 1.02, 23.2, 23.31, 31.06

(56) References Cited

U.S. PATENT DOCUMENTS

| | | |
|---|---|---|
| 4,007,435 A | 2/1977 | Tien |
| 4,151,503 A | 4/1979 | Cermak et al. |
| 4,225,842 A | 9/1980 | Schlesselman et al. |
| 4,234,542 A | 11/1980 | Romine |
| 4,387,359 A | 6/1983 | Tien et al. |
| 4,457,161 A | 7/1984 | Iwanaga et al. |
| 4,535,316 A | 8/1985 | Wertheimer et al. |
| 4,542,640 A | 9/1985 | Clifford |
| 4,770,760 A | 9/1988 | Noda et al. |
| 5,239,483 A | 8/1993 | Weir |

(List continued on next page.)

FOREIGN PATENT DOCUMENTS

| | | |
|---|---|---|
| DE | 4 228 052 | 4/1993 |
| DE | 4408361 | 9/1995 |
| DE | 4408504 | 9/1995 |
| DE | 201 01 638 | 5/2001 |
| EP | 293 255 | 11/1988 |
| EP | 527 258 | 2/1993 |
| EP | 1 286 155 | 2/2003 |
| JP | 09005273 | 1/1997 |
| JP | 10062374 | 3/1998 |
| JP | 10260155 | 9/1998 |
| JP | 10267895 | 10/1998 |
| JP | 2001281185 | 10/2001 |
| WO | WO 0000808 | 1/2000 |
| WO | WO 0233393 | 4/2002 |
| WO | WO 03/087550 | 10/2003 |

OTHER PUBLICATIONS

S.W. Moore, et al., A modified multilayer perceptron model for gas mixture analysis, Sensors and Actuators B, 15–16 (1993) pp. 344–348, Elsevier Sequoia.

(List continued on next page.)

Primary Examiner—Jill Warden
Assistant Examiner—Brian J. Sines

(57) ABSTRACT

Disclosed herein is a method and apparatus for analyzing, sensing and measuring information related to the concentrations of various gases, including $NO_x$, hydrocarbons, carbon monoxide and oxygen, in a multi-component gas system using chemical sensors and chemical sensor arrays. The sensors and sensor arrays use chemo/electro-active materials to analyze and detect the presence of gases.

136 Claims, 3 Drawing Sheets

U.S. PATENT DOCUMENTS

| | | | |
|---|---|---|---|
| 5,426,934 | A | 6/1995 | Hunt et al. |
| 5,554,273 | A | 9/1996 | Demmin et al. |
| 5,571,401 | A * | 11/1996 | Lewis et al. ............... 205/787 |
| 5,630,920 | A | 5/1997 | Friese et al. |
| 5,731,510 | A | 3/1998 | Jones et al. |
| 5,736,028 | A | 4/1998 | Hjortsberg et al. |
| 5,776,601 | A | 7/1998 | Fournier et al. |
| 5,832,411 | A | 11/1998 | Schatzmann et al. |
| 5,879,526 | A | 3/1999 | Dietz et al. |
| 6,006,586 | A | 12/1999 | Yoshida et al. |
| 6,012,282 | A | 1/2000 | Kato et al. |
| 6,041,592 | A | 3/2000 | Huynh et al. |
| 6,082,176 | A | 7/2000 | Kondo et al. |
| 6,084,418 | A | 7/2000 | Takami et al. |
| 6,085,576 | A | 7/2000 | Sunshine et al. |
| 6,109,095 | A | 8/2000 | Addiego |
| 6,149,786 | A | 11/2000 | Patrick et al. |
| 6,170,318 | B1 | 1/2001 | Lewis |
| 6,235,243 | B1 | 5/2001 | Fleischer et al. |
| 6,238,536 | B1 | 5/2001 | Lundgren et al. |
| 6,306,351 | B1 | 10/2001 | Kudo et al. |
| 6,367,320 | B1 | 4/2002 | Kueper et al. |
| 6,411,905 | B1 | 6/2002 | Guoliang et al. |
| 6,498,046 | B2 | 12/2002 | McCarron et al. |
| 6,592,823 | B1 | 7/2003 | Odermatt et al. |
| 2002/0017467 | A1 | 2/2002 | Ando et al. |

OTHER PUBLICATIONS

H. Meixner, et al., Metal oxide sensors, Sensors and Actuators B 33 (1996) pp. 198–202, Elsevier Science.

J. Getino, et al., Integrated sensor array for gas analysis in combustion atmospheres, Sensors and Actuators B 33 (1996) pp. 128–133, Elsevier Science.

Corrado Di Natale, et al., Study of the effect of the sensor operating temperature on $SnO_2$–based sensor–array performance, Sensors and Actuators B 23 (1995) pp. 187–191, Elsevier Science.

Brent T. Marquis, et al., A semiconducting metal oxide sensor array for the detection of $NO_x$ and $NH_3$, Sensors and Actuators B 77 (2001) pp. 100–110, Elsevier Science.

G. Huyberechts, et al., Simultaneous quantification of carbon monoxide and methane in humid air using a sensor array and an artificial neural network, Sensors and Actuators B 45 (1997) pp. 123–130, Elsevier Science.

Kazimierz Brudzewski, et al., Gas analysis system composed of a solid–state sensor array and hybrid neural network structure, Sensors and Actuators B 55 (1999) pp. 38–46, Elsevier Science.

P.C. Jurs, et al., Computational methods for the analysis of chemical sensor array data from volatile analytes, Chem Rev. 2000, 100, pp. 2649–2678, American Chemical Society.

Keith J. Albert, et al., Cross–reactive chemical sensor arrays, Chem. Rev. 2000, 100, pp. 2595–2626, American Chemical Society.

P. Vincenzini, et al., Solid state chemical and biochemical sensors, Advances in Science and Technology, 26, pp. 335–345, National Research Center, Italy.

Antonio Parado, et al., Nonlinear inverse dynamic models of gas sensing systems based on chemical sensor arrays for quantitative measurements, IEEE Transactions on Instrumentation and Measurement, vol. 47, No. 3, Jun. 1998, pp. 644–651.

BS Hoffheins, et al., Performance of simplified chemical sensor arrays in a neural network–based analytical instrument, Analysis (1992) 20, pp. 201–207, Elsevier, Paris.

Corrado Di Natale, et al., Performance evaluation of an $SnO_2$–based sensor array for the quantitative measurement of mixtures of $H_2S$ and $NO_2$, Sensors and Actuators B, 20 (1994) pp. 217–224.

H. Meixner, et al., Chemosensors for motor management systems of the future, Fresenius J. Anal Chem. (1994) 348, pp. 536–541.

Marquis, A Semiconducting metal oxide sensor array for the detection of $NO_x$ and $NH_3$, Sensors and Actuators B 77 (2001), pp. 100–110, Orono, ME.

* cited by examiner

METHOD AND APPARATUS FOR ANALYZING MIXTURES OF GASES

This application is a continuation-in-part of U.S. application Ser. No. 09/977,791, filed Oct. 15, 2001 (which is incorporated in its entirety as a part hereof), which claimed the benefit of U.S. Provisional Application No. 60/240,619, filed Oct. 16, 2000, and U.S. Provisional Application No. 60/246,946, filed Nov. 9, 2000.

FIELD OF THE INVENTION

The present invention is a method and apparatus for sensing and analyzing certain gases, including $NO_x$, hydrocarbons, carbon monoxide and oxygen in a multi-component gas system using chemical sensors and chemical sensor arrays. The sensors and sensor arrays use chemo/electro-active materials to detect the presence of and/or calculate the concentration of individual gases within the multi-component gas system.

TECHNICAL BACKGROUND

The use of chemical sensing devices to detect certain gases is known. Many attempts have been made to find a material with selectivity and sensitivity for a specific gas. For example, U.S. Pat. No. 4,535,316 discloses a resistive sensor for measuring oxygen. See also H. Meixner et al, *Sensors and Actuators*, B 33 (1996) 198–202. It is apparent that different materials must be used for each gas to be detected. However, when a gas is part of a multi-component system, using one material to detect a specific gas is difficult because of the cross-sensitivities of the material to the various component gases of the mixture.

One example of a multi-component gaseous system is a combustion gas emission, which can include oxygen, carbon monoxide, nitrogen oxides, hydrocarbons, $CO_2$, $H_2S$, sulfur dioxide, hydrogen, water vapor, halogens and ammonia. See H. Meixner et al, *Fresenius' J. Anal. Chem.*, 348 (1994) 536–541. In many combustion processes, there is a need to determine whether the gas emissions meet requirements established by federal and state air quality regulations in various jurisdictions. Several types of gas sensors have been developed to address this need. See U.S. Pat. No. 5,630,920, Friese et al, which discloses an electrochemical oxygen sensor; U.S. Pat. No. 4,770,760, Noda et al, which discloses a sensor for detecting oxygen and oxides of nitrogen; and U.S. Pat. No. 4,535,316, which discloses a resistive sensor for measuring oxygen. It would be advantageous to be able to simultaneously analyze two or more components of a mixture such as a combustion gas emission, to calculate concentration for example, in terms only of data generated by direct contact of the gases with a sensor and without having to separate any of the gases in the mixture. Prior art methods do not currently meet this need.

Numerous sensors have been disclosed to detect gases evolving from foods and from other relatively low temperature applications. See K. Albert et al, *Chem. Rev.*, 200 (2000) 2595–2626. Arrays of several undoped and doped tin oxide sensors have also been disclosed for use in detecting various combustion gases up to 450° C. See C. Di Natale et al, *Sensors and Actuators*, B 20 (1994) 217–224; J. Getino et al, *Sensors and Actuators*, B33 (1996) 128–133; and C. Di Natale et al, *Sensors and Actuators*, B 23 (1995) 187–191. However, at higher temperatures and in the highly corrosive environment in which one would use chemical sensors to monitor combustion gases, operating temperature can alter or impair the performance of the sensor array. That being the case, high temperature environments require the use of materials that are both chemically and thermally stable and that maintain measurable responses to the gases of interest. The effect of the operating temperature on the response of tin oxide bases sensor arrays was studied up to 450° C. See C. Di Natale, *Sensors and Actuators* B23 (1995) 187–191. However, materials in addition to those previously known in the art are still needed to be able to provide a method and apparatus capable of directly monitoring the gas emissions of multi-component gas systems at higher temperatures, such as would be encountered in the operation of combustion gas systems.

Addressing this need would permit the use of a chemical sensor to measure combustion emissions, such as automobile exhausts, and determine whether those emissions meet functional and mandated requirements. In addition, it has surprisingly been found that the method and apparatus of this invention that are useful for analyzing high temperature gases, such as automotive emissions, may be employed with equal effect in analyzing low temperature gases.

SUMMARY OF THE INVENTION

This invention provides a method for directly sensing gas components in a multi-component gas system, comprising the steps of: (i) exposing a chemical sensor comprising an array of at least two chemo/electro-active materials to a multi-component gas system, detecting a response, and directly measuring the response of each chemo/electro-active material. Preferably the chemo/electro-active material is a semiconducting material, and the multi-component gas system is a combustion process emission. The response that is measured can be a measurement of capacitance, voltage, current, AC impedance, or DC resistance.

This invention also provides a chemical sensor for directly sensing the presence of gas components in a multi-component gas system, comprising a substrate; an array of at least two chemo/electro-active materials on said substrate; and a means for detecting a response from said chemo/electro-active materials when exposed to said analyte gas component(s) in the system. Preferably the chemo/electro-active material is a semiconducting material, and the multi-component gas system is a combustion process emission. The response that is detected can be an electrical property such as capacitance, voltage, current, AC impedance, or DC resistance. The device can additionally contain a housing, means for measuring the detected responses, and means for analyzing the results of the measured responses in order to identify the presence and/or concentrations of the analyte gas components(s).

This invention also provides for a chemical sensor device for directly sensing the presence and/or concentration of gas component(s) in a multi-component gas system, comprising: a substrate; an array of at least two chemo/electro-active materials deposited on said substrate; a means for detecting a change in electrical properties of said chemo/electro-active materials upon exposure to said multi-component gas component(s); means for analyzing the results of the detected changes in electrical properties in order to identify the presence and/or concentrations of said gas component(s); and a housing. The chemo/electro-active materials may be semiconducting materials.

Another embodiment of this invention is a gas-sensitive apparatus that includes an array of at least three chemo/electro-active materials, each chemo/electro-active material exhibiting a change in electrical resistance upon exposure to a multi-component gas mixture, wherein at least one chemo/ electro-active material, when at a temperature of about 400° C. or more, (a) has an electrical resistivity in the range of about 1 ohm-cm to about $10^6$ ohm-cm, and (b) exhibits a change in electrical resistance of at least about 0.1 percent upon exposure of the material to the gas mixture, as compared to the resistance before exposure. Yet another embodiment of this invention is an apparatus for analyzing a multi-component gas mixture that includes an array as described above and means for determining an electrical response of the chemo/electro-active materials upon exposure of the array to the gas mixture.

Yet another embodiment of this invention is a gas-sensitive apparatus that includes an array of at least two chemo/electro-active materials, each chemo/electro-active material exhibiting a different electrical response characteristic upon exposure at a selected temperature to a multi-component gas mixture than each of the other chemo/electro-active materials, the electrical response characteristic of at least one material being quantifiable as a value, wherein the value of the response of that material is constant or varies by no more than about twenty percent during exposure of the material to the gas mixture at the selected temperature for a period of at least about one minute. Yet another embodiment of this invention is an apparatus for analyzing a multi-component gas mixture that includes an array as described above and means for determining an electrical response of the chemo/electro-active materials upon exposure of the array to the gas mixture.

Yet another embodiment of this invention is an array of chemo/electro-active materials, each chemo/electro-active material exhibiting a different electrical response characteristic, upon exposure at a selected temperature to a multi-component gas mixture, than each of the other chemo/electro-active materials, wherein at least one chemo/electro-active materials is selected from the group consisting of $M^1O_x$, $M^1_aM^2_bO_x$ and $M^1_aM^2_bM^3_cO_x$; wherein $M^1$ is selected from the group consisting of Ce, Co, Cu, Fe, Ga, Nb, Ni, Pr, Ru, Sn, Ti, Tm, W, Yb, Zn, and Zr; $M^2$ and $M^3$ are each independently selected from the group consisting of Al, Ba, Bi, Ca, Cd, Ce, Co, Cr, Cu, Fe, Ga, Ge, In, K, La, Mg, Mn, Mo, Na, Nb, Ni, Pb, Pr, Rb, Ru, Sb, Sc, Si, Sn, Sr, Ta, Ti, Tm, V, W, Y, Yb, Zn, and Zr, but $M^2$ and $M^3$ are not the same in $M^1_aM^2_bM^3_cO_x$; a, b and c are each independently about 0.0005 to about 1; and x is a number sufficient so that the oxygen present balances the charges of the other elements in the compound. Yet another embodiment of this invention is an apparatus for analyzing a multi-component gas mixture that includes an array as described above and means for determining an electrical response of the chemo/electro-active materials upon exposure of the array to the gas mixture.

Yet another embodiment of this invention is a gas-sensitive apparatus that includes an array of first and second chemo/electro-active materials, each chemo/electro-active material exhibiting a different electrical response characteristic upon exposure at a selected temperature to a multi-component gas mixture than each of the other chemo/electro-active materials, wherein the chemo/electro-active materials are selected from the pairings in the group consisting of (i) the first material is $M^1O_x$, and the second material is $M^1_aM^2_bO_x$;

(ii) the first material is $M^1O_x$, and the second material is $M^1_aM^2_bM^3_cO_x$;

(iii) the first material is $M^1_aM^2_bO_x$, and the second material is $M^1_aM^2_bM^3_cO_x$;

(iv) the first material is a first $M^1O_x$, and the second material is a second $M^1O_x$;

(v) the first material is a first $M^1_aM^2_bO_x$, and the second material is a second $M^1_aM^2_bO_x$; and (vi) the first material is a first $M^1_aM^2_bM^3_cO_x$, and the second material is a second $M^1_aM^2_bM^3_cO_x$;

wherein $M^1$ is selected from the group consisting of Ce, Co, Cu, Fe, Ga, Nb, Ni, Pr, Ru, Sn, Ti, Tm, W, Yb, Zn, and Zr; $M^2$ and $M^3$ are each independently selected from the group consisting of Al, Ba, Bi, Ca, Cd, Ce, Co, Cr, Cu, Fe, Ga, Ge, In, K, La, Mg, Mn, Mo, Na, Nb, Ni, Pb, Pr, Rb, Ru, Sb, Sc, Si, Sn, Sr, Ta, Ti, Tm, V, W, Y, Yb, Zn, and Zr, but $M^2$ and $M^3$ are not the same in $M^1_aM^2_bM^3_cO_x$; a, b and c are each independently about 0.0005 to about 1; and x is a number sufficient so that the oxygen present balances the charges of the other elements in the compound. Yet another embodiment of this invention is an apparatus for analyzing a multi-component gas mixture that includes an array as described above and means for determining an electrical response of the chemo/electro-active materials upon exposure of the array to the gas mixture.

Yet another embodiment of this invention is an apparatus for analyzing a multi-component gas mixture that includes (a) an array of at least two chemo/electro-active materials, each chemo/electro-active material exhibiting a different electrical response characteristic, upon exposure to the gas mixture, than each of the other chemo/electro-active materials; and (b) means for determining an electrical response of each chemo/electro-active material individually upon exposure of the array to the gas mixture. The apparatus may optionally also include means for measuring the temperature of the array, and means for digitizing the electrical responses and the temperature measurement.

Yet another embodiment of this invention is an apparatus for calculating the concentration of at least two individual analyte gas components in a multi-component gas mixture including (a) an array of at least three chemo/electro-active materials, each chemo/electro-active material exhibiting a different electrical response characteristic, upon exposure to the gas mixture, than each of the other chemo/electro-active materials; (b) means for determining an electrical response of each chemo/electro-active material upon exposure of the array to only the unseparated components of the gas mixture; (c) means for calculating the concentration of an individual analyte gas component from the electrical responses of the chemo/electro-active materials.

Yet another embodiment of this invention is an apparatus for analyzing a multi-component gas mixture including (a) an array of at least three chemo/electro-active materials, each chemo/electro-active material exhibiting a different electrical response characteristic, upon exposure to the gas mixture, than each of the other chemo/electro-active materials; (b) means for determining an electrical response of each chemo/electro-active material upon exposure of the array to the gas mixture; and (c) means for (i) detecting the presence of a subgroup of gases in the mixture from the responses of a first group of at least two chemo/electro-active materials, and (ii) detecting the presence of an individual component gas in the mixture from the responses of a second group of at least two chemo/electro-active materials.

Yet another embodiment of this invention involves a method for analyzing a multi-component gas mixture, including the steps of:

(a) providing an array of at least two chemo/electro-active materials, each chemo/electro-active material exhibiting a different electrical response characteristic upon exposure to the gas mixture than each other chemo/electro-active material;

(b) exposing the array to the gas mixture;

(c) determining an electrical response of each chemo/electro-active material individually upon exposure of the array to the gas mixture;

(d) measuring the temperature of the gas mixture independently of the determination of the electrical responses of the chemo/electro-active materials; and (e) digitizing the electrical responses and the temperature measurement.

Yet another embodiment of this invention involves a method for calculating the concentration of at least two individual analyte gas components in a multi-component gas mixture having a temperature of about 400° C. or more, including the steps of:

(a) providing within the gas mixture an array of at least three chemo/electro-active materials, each chemo/electro-active material exhibiting a different electrical response characteristic upon exposure to the gas mixture than each of the other chemo/electro-active materials, wherein at least one chemo/electro-active material, when at a temperature of about 400° C. or more, (i) has an electrical resistivity in the range of about 1 ohm-cm to about $10^6$ ohm-cm, and (ii) exhibits a change in electrical resistance of at least about 0.1 percent upon exposure of the material to the gas mixture, as compared to the resistance before exposure;

(b) determining an electrical response of each chemo/electro-active material upon exposure of the array to the unseparated components of the gas mixture; and (c) calculating the concentration of each of the individual analyte gas components from the electrical responses of the chemo/electro-active materials.

Yet another embodiment of this invention involves a method for analyzing a multi-component gas mixture, including the steps of:

(a) providing an array of at least two chemo/electro-active materials, each chemo/electro-active material exhibiting a different electrical response characteristic upon exposure at a selected temperature to the gas mixture than each of the other chemo/electro-active materials, the electrical response characteristic of at least one material being quantifiable as a value, wherein the value of the response of that material is constant or varies by no more than about twenty percent during exposure of the material to the gas mixture at the selected temperature for a period of at least about one minute; and (b) determining the electrical response of each chemo/electro-active material upon exposure of the array to the gas mixture.

Yet another embodiment of this invention is a method for analyzing a multi-component gas mixture by (a) providing an array of at least three chemo/electro-active materials, each chemo/electro-active material exhibiting a different electrical response characteristic, upon exposure to the gas mixture, than each of the other chemo/electro-active materials; (b) determining an electrical response of each chemo/electro-active material upon exposure of the array to the gas mixture; and (c) detecting (i) the presence of a subgroup of gases in the mixture from the responses of a first group of at least two chemo/electro-active materials, and (ii) the presence of an individual component gas in the mixture from the responses of a second group of at least two chemo/electro-active materials.

DETAILED DESCRIPTION OF THE INVENTION

The present invention is a method and apparatus for directly sensing one or more analyte gases in a multi-component gas system under variable temperature conditions. By "directly sensing" is meant that an array of gas-sensing materials will be exposed to a mixture of gases that constitutes a multi-component gas system, such as in a stream of flowing gases. The array may be situated within the gas mixture, and more particularly within the source of the gas mixture, if desired. Alternatively, the array may reside in a chamber to which the gas mixture is directed from its source at another location. When gas is directed to a chamber in which an array is located, the gas mixture may be inserted in and removed from the chamber by piping, conduits or any other suitable gas transmission equipment.

A response may be obtained upon exposure of the gas-sensing materials to the multi-component gas mixture, and the response will be a function of the concentrations of one or more of the analyte gases themselves in the gas mixture. The sensor materials will be exposed substantially simultaneously to each of the analyte gases, and an analyte gas does not have to be physically separated from the multi-component gas mixture for an analysis of the mixture and/or one or more components thereof to be conducted. This invention can be used, for example, to detect and/or measure the concentrations of combustion gases, such as oxygen, carbon monoxide, nitrogen oxides, hydrocarbons such as butane, $CO_2$, $H_2S$, sulfur dioxide, halogens, hydrogen, water vapor and ammonia, at variable temperatures in automobile emissions.

This invention is therefore useful at the higher temperatures found in automotive emission systems, typically in the range of from about 400° C. to about 1000° C. In addition there are a variety of other combustion processes for which this invention could be applied, including diesel engines and home heating. These applications require the detection of gases such as nitrogen oxides, ammonia, carbon monoxide, hydrocarbons and oxygen at the ppm to per cent levels, typically in a highly corrosive environment. This invention is also useful for detecting gases in other gas systems such as those found in manufacturing processes, waste streams, and environmental monitoring; or in systems in which odor detection is important and/or that are at lower temperature, such as in the medical, agricultural or food and beverage industries.

Figure 1:
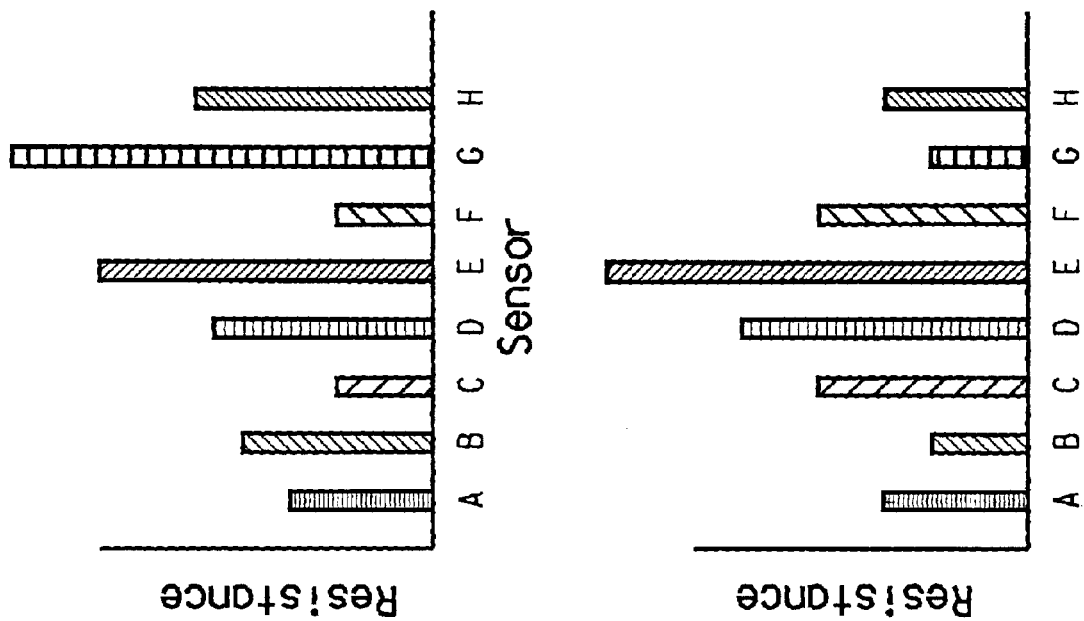
FIG. 1 depicts an array of chemo/electro-active materials.
Figure 1:
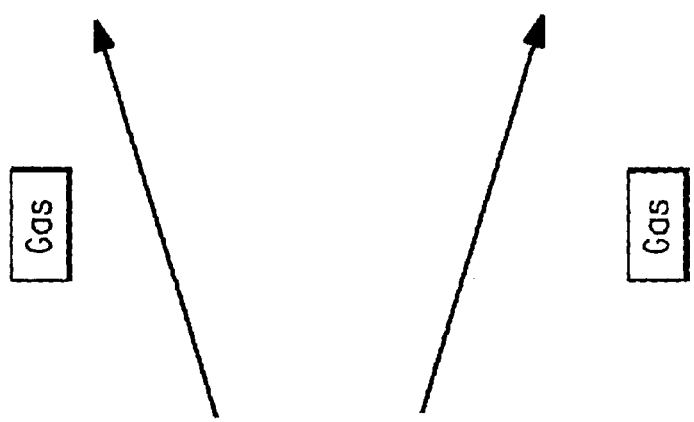
Figure 1:
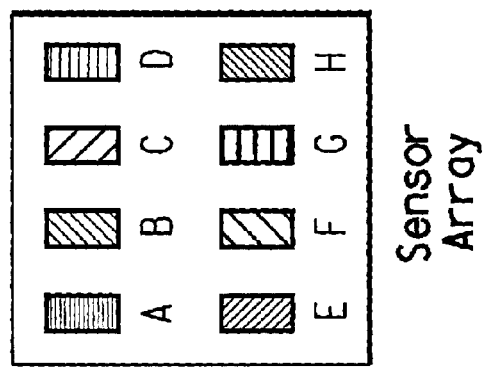

This invention utilizes an array of sensing materials to analyze a gas mixture and/or the components thereof to, for example, detect the presence of and/or calculate the concentration of one or more individual analyte gas components in the system. By "array" is meant at least two different materials that are spatially separated, as shown for example in FIG. 1. The array may contain, for example, 3, 4, 5, 6, 8, 10 or 12 gas-sensing materials, or other greater or lesser numbers as desired. It is preferred that there be provided at least one sensor material for each of the individual gases or subgroups in the mixture to be analyzed. It may be desirable, however, to provide more than one sensor material that is responsive to an individual gas component and/or a particular subgroup in the mixture. For example, a group of at least 2, 3, 4, 5, 6, 7, 8, 9, 10, 11 or 12 sensors could be used to detect the presence of, and/or calculate the concentration of, one or more individual component gases and/or one or more subgroups of gases in the mixture. Different groups of sensors could be used for this purpose, which may or may not have members in common. A subgroup of gases that is an analyte as the subgroup may or may not contain as a member an individual gas that is itself an analyte. Preferably the mole percentages of the major components of each gas-sensing material differs from that of each of the others.

The sensing materials used are chemo/electro-active materials. A "chemo/electro-active material" is a material that has an electrical response to at least one individual gas in a mixture. Some metal oxide semiconducting materials, mixtures thereof, or mixtures of metal oxide semiconductors with other inorganic compounds are chemo/electro-active, and are particularly useful in this invention. Each of the various chemo/electro-active materials used herein preferably exhibits an electrically-detectable response of a different kind and/or extent, upon exposure to the mixture and/or an analyte gas, than each of the other chemo/electro-active materials. As a result, an array of appropriately chosen chemo/electro-active materials can be used to analyze a multi-component gas mixture, such as by interacting with an analyte gas, sensing an analyte gas, or determining the presence and/or concentration of one or more analyte gases in a mixture, despite the presence therein of interfering gases that are not of interest.

This invention is useful for detecting those gases that are expected to be present in a gas stream. For example, in a combustion process, gases that are expected to be present include oxygen, nitrogen oxides (such as NO, $NO_2$, $N_2O$ or $N_2O_4$), carbon monoxide, hydrocarbons (such as $C_nH_{2n+2}$, and as same may be saturated or unsaturated, or be optionally substituted with hetero atoms; and cyclic and aromatic analogs thereof), ammonia or hydrogen sulfide, sulfur dioxide, $CO_2$, or methanol. Other gases of interest may include alcohol vapors, solvent vapors, hydrogen, water vapor, and those deriving from saturated and unsaturated hydrocarbons, ethers, ketones, aldehydes, carbonyls, biomolecules and microorganisms. The component of a multi-component gas mixture that is an analyte of interest may be an individual gas such as carbon monoxide; may be a subgroup of some but not all of the gases contained in the mixture, such as the nitrogen oxides ($NO_x$); or may be a combination of one or more individual gases and one or more subgroups. When a subgroup of gases is an analyte, a chemo/electro-active material will respond to the collective concentration within a multi-component gas mixture of the members of the subgroup together.

Obtaining information related to the compositional content of a gas mixture using these sensor materials, such as measurement of gas concentrations, can be based on a change in an electrical property, such as AC impedance, of at least one, but preferably each and all, of the materials upon exposure of the materials to a mixture containing one or more analyte gases. Analysis of a gas mixture can also be performed in terms of extent of change in other electrical properties of the sensor materials, such as capacitance, voltage, current or AC or DC resistance. Change in DC resistance may be determined, for example, by measuring change in temperature at constant voltage. The change in one of these illustrative properties of a sensor material is a function of the partial pressure of an analyte gas within the gas mixture, which in turn determines the concentration at which the molecules of the analyte gases become adsorbed on the surface of a sensor material, thus affecting the electrical response characteristics of that material. By using an array of chemo/electro-active materials, a pattern of the respective responses exhibited by the materials upon exposure to a mixture containing one or more analyte gases can be used to simultaneously and directly detect the presence of, and/or measure the concentration of, at least one gas in a multi-component gas system. The invention, in turn, can be used to determine the composition of the gas system. The concept is illustrated schematically in FIG. 1 and is exemplified below.

To illustrate, consider the theoretical example below of the exposure of a sensor material to a mixture containing an analyte gas. Where a response is obtanied, the event is depicted as positive (+), and where no response is obtained, the event is depicted as negative (−). Material 1 responds to Gas 1 and Gas 2, but shows no response to Gas 3. Material 2 responds to Gas 1 and Gas 3, but shows no response to Gas 2, and Material 3 responds to Gas 2 and Gas 3, but shows no response to Gas 1.

|  | Material 1 | Material 2 | Material 3 |
| --- | --- | --- | --- |
| Gas 1 | + | + | − |
| Gas 2 | + | − | + |
| Gas 3 | − | + | + |

Therefore, if an array consisting of Materials 1, 2 and 3 gives the following response to an unknown gas,

|  | Material 1 | Material 2 | Material 3 |
| --- | --- | --- | --- |
| Unknown Gas | + | − | + | then the unknown gas would be identified as Gas 2. The response of each sensor material would be a function of the partial pressure within the mixture of, and thus the concentration of, an analyte gas or the collective concentration of a subgroup of analyte gases; and the response could be quantified or recorded as a processible value, such as a numerical value. In such case, the values of one or more responses can be used to generate quantitative information about the concentration within the mixture of one or more analyte gases. In a multicomponent gas system, chemometrics, neural networks or other pattern recognition techniques could be used to calculate the concentration of one or more analyte gases in the mixture of the system.

The chemo/electro-active material can be of any type, but especially useful are semiconducting metal oxides such as ZnO, $TiO_2$, $WO_3$, and $SnO_2$. These particular materials are advantageous due to their chemical and thermal stability. The chemo/electro-active material can be a mixture of two or more semiconducting materials, or a mixture of a semiconducting material with an inorganic material, or combinations thereof. The semiconducting materials of interest can be deposited on a suitable solid substrate that is an insulator such as, but not limited to, alumina or silica and is stable under the conditions of the multi-component gas mixture. The array then takes the form of the sensor materials as deposited on the substrate. Other suitable sensor materials include single crystal or polycrystalline semiconductors of the bulk or thin film type, amorphous semiconducting materials, and semiconductor materials that are not composed of metal oxides.

The chemo/electro-active materials used as sensor materials in this invention may, for example, be metal oxides of the formula $M^1O_x$, $M^1_aM^2_bO_x$, or $M^1_aM^2_bM^3_cO_x$; or mixtures thereof, wherein $M^1$, $M^2$ and $M^3$ are metals that form stable oxides when fired in the presence of oxygen above 500° C.;

$M^1$ is selected from Periodic Groups 2–15 and the lanthanide group;

$M^2$ and $M^3$ are independently selected from Periodic Groups 1–15 and the lanthanide group, but $M^2$ and $M^3$ are not the same in $M^1_aM^2_bM^3_cO_x$;

a, b, and c are each independently in the range of about 0.0005 to about 1; and x is a number sufficient so that the oxygen present balances the charges of the other elements in the compound.

The metal oxides that contain more than one metal do not have to be a compound or solid solution, but can be a mixture of discrete metal oxides. They may exhibit composition gradients, and can be crystalline or amorphous. Suitable metal oxides are those that 1) when at a temperature of about 400° C. or above, have a resistivity of about 1 to about $10^6$ ohm-cm, preferably about 1 to about $10^5$ ohm-cm, and more preferably about 10 to about $10^4$ ohm-cm, 2) show a chemo/electro response to at least one gas of interest, and 3) are stable and have mechanical integrity, that is are able to adhere to the substrate and not degrade at the operating temperature.

The metal oxides may also contain minor or trace amounts of hydration and elements present in the precursor materials.

In certain preferred embodiments, the metal oxide materials may include those in which $M^1$ is selected from the group consisting of Ce, Co, Cu, Fe, Ga, Nb, Ni, Pr, Ru, Sn, Ti, Tm, W, Yb, Zn, and Zr; and/or $M^2$ and $M^3$ are each independently selected from the group consisting of Al, Ba, Bi, Ca, Cd, Ce, Co, Cr, Cu, Fe, Ga, Ge, In, K, La, Mg, Mn, Mo, Na, Nb, Ni, Pb, Pr, Rb, Ru, Sb, Sc, Si, Sn, Sr, Ta, Ti, Tm, V, W, Y, Yb, Zn, and Zr, but $M^2$ and $M^3$ are not the same in $M^1_aM^2_bM^3_cO_x$.

In certain other preferred embodiments, the metal oxide materials may include those in which $M^1O_x$ is $Ce_aO_x$, $CoO_x$, $CuO_x$, $FeO_x$, $GaO_x$, $NbO_x$, $NiO_x$, $PrO_x$, $RuO_x$, $SnO_x$, $Ta_aO_x$, $TiO_x$, $TmO_x$, $WO_x$, $YbO_x$, $ZnO_x$, $ZrO_x$, $SnO_x$ with Ag additive, $ZnO_x$ with Ag additive, $TiO_x$ with Pt additive, $ZnO_x$ with frit additive, $NiO_x$ with frit additive, $SnO_x$ with frit additive, or $WO_x$ with frit additive; and/or $M^1_aM^2_bO_x$ is $Al_aCr_bO_x$, $Al_aFe_bO_x$, $Al_aMg_bO_x$, $Al_aNi_bO_x$, $Al_aTi_bO_x$, $Al_aV_bO_x$, $Ba_aCu_bO_x$, $Ba_aSn_bO_x$, $Ba_aZn_bO_x$, $Bi_aRu_bO_x$, $Bi_aSn_bO_x$, $Bi_aZn_bO_x$, $Ca_aSn_bO_x$, $Ca_aZn_bO_x$, $Cd_aSn_bO_x$, $Cd_aZn_bO_x$, $Ce_aFe_bO_x$, $Ce_aNb_bO_x$, $Ce_aTi_bO_x$, $Ce_aV_bO_x$, $Co_aCu_bO_x$, $Co_aGe_bO_x$, $Co_aLa_bO_x$, $Co_aMg_bO_x$, $Co_aNb_bO_x$, $Co_aPb_bO_x$, $Co_aSn_bO_x$, $Co_aV_bO_x$, $Co_aW_bO_x$, $Co_aZn_bO_x$, $Cr_aCu_bO_x$, $Cr_aLa_bO_x$, $Cr_aMn_bO_x$, $Cr_aNi_bO_x$, $Cr_aSi_bO_x$, $Cr_aTi_bO_x$, $Cr_aY_bO_x$, $Cr_aZn_bO_x$, $Cu_aFe_bO_x$, $Cu_aGa_bO_x$, $Cu_aLa_bO_x$, $Cu_aNa_bO_x$, $Cu_aNi_bO_x$, $Cu_aPb_bO_x$, $Cu_aSn_bO_x$, $Cu_aSr_bO_x$, $Cu_aTi_bO_x$, $Cu_aZn_bO_x$, $Cu_aZr_bO_x$, $Fe_aGa_bO_x$, $Fe_aLa_bO_x$, $Fe_aMo_bO_x$, $Fe_aNb_bO_x$, $Fe_aNi_bO_x$, $Fe_aSn_bO_x$, $Fe_aTi_bO_x$, $Fe_aW_bO_x$, $Fe_aZn_bO_x$, $Fe_aZr_bO_x$, $Ga_aLa_bO_x$, $Ga_aSn_bO_x$, $Ge_aNb_bO_x$, $Ge_aTi_bO_x$, $In_aSn_bO_x$, $K_aNb_bO_x$, $Mn_aNb_bO_x$, $Mn_aSn_bO_x$, $Mn_aTi_bO_x$, $Mn_aY_bO_x$, $Mn_aZn_bO_x$, $Mo_aPb_bO_x$, $Mo_aRb_bO_x$, $Mo_aSn_bO_x$, $Mo_aTi_bO_x$, $Mo_aZn_bO_x$, $Nb_aNi_bO_x$, $Nb_aNi_bO_x$, $Nb_aSr_bO_x$, $Nb_aTi_bO_x$, $Nb_aW_bO_x$, $Nb_aZr_bO_x$, $Ni_aSi_bO_x$, $Ni_aSn_bO_x$, $Ni_aY_bO_x$, $Ni_aZn_bO_x$, $Ni_aZr_bO_x$, $Pb_aSn_bO_x$, $Pb_aZn_bO_x$, $Rb_aW_bO_x$, $Ru_aSn_bO_x$, $Ru_aW_bO_x$, $Ru_aZn_bO_x$, $Sb_aSn_bO_x$, $Sb_aZn_bO_x$, $Sc_aZr_bO_x$, $Si_aSn_bO_x$, $Si_aTi_bO_x$, $Si_aW_bO_x$, $Si_aZn_bO_x$, $Sn_aTa_bO_x$, $Sn_aTi_bO_x$, $Sn_aW_bO_x$, $Sn_aZn_bO_x$, $Sn_aZr_bO_x$, $Sr_aTi_bO_x$, $Ta_aTi_bO_x$, $Ta_aZn_bO_x$, $Ta_aZr_bO_x$, $Ti_aV_bO_x$, $Ti_aW_bO_x$, $Ti_aZn_bO_x$, $Ti_aZr_bO_x$, $V_aZn_bO_x$, $V_aZr_bO_x$, $W_aZn_bO_x$, $W_aZr_bO_x$, $Y_aZr_bO_x$, $Zn_aZr_bO_x$, $Al_aNi_bO_x$ with frit additive, $Cr_aTi_bO_x$ with frit additive, $Fe_aLa_bO_x$ with frit additive, $Fe_aNi_bO_x$ with frit additive, $Fe_aTi_bO_x$ with frit additive, $Nb_aTi_bO_x$ with frit additive, $Nb_aW_bO_x$ with frit additive, $Ni_aZn_bO_x$ with frit additive, $Ni_aZr_bO_x$ with frit additive, $Sb_aSn_bO_x$ with frit additive, $Ta_aTi_bO_x$ with frit additive, or $Ti_aZn_bO_x$ with frit additive; and/or $M^1_aM^2_bM^3_cO_x$ is $Al_aMg_bZn_cO_x$, $Al_aSi_bV_cO_x$, $Ba_aCu_bTi_cO_x$, $Ca_aCe_bZr_cO_x$, $Co_aNi_bTi_cO_x$, $Co_aNi_bZr_cO_x$, $Co_aPb_bSn_cO_x$, $Co_aPb_bZn_cO_x$, $Cr_aSr_bTi_cO_x$, $Cu_aFe_bMn_cO_x$, $Cu_aLa_bSr_cO_x$, $Fe_aNb_bTi_cO_x$, $Fe_aPb_bZn_cO_x$, $Fe_aSr_bTi_cO_x$, $Fe_aTa_bTi_cO_x$, $Fe_aW_bZr_cO_x$, $Ga_aTi_bZn_cO_x$, $La_aMn_bNa_cO_x$, $La_aMn_bSr_cO_x$, $Mn_aSr_bTi_cO_x$, $Mo_aPb_bZn_cO_x$, $Nb_aSr_bTi_cO_x$, $Nb_aSr_bW_cO_x$, $Nb_aTi_bZn_cO_x$, $Ni_aSr_bTi_cO_x$, $Sn_aW_bZn_cO_x$, $Sr_aTi_bV_cO_x$, $Sr_aTi_bZn_cO_x$, or $Ti_aW_bZr_cO_x$.

In certain other preferred embodiments, the metal oxide materials may include those that are in an array of first and second chemo/electro-active materials, wherein the chemo/electro-active materials are selected from the pairings in the group consisting of (i) the first material is $M^1O_x$, and the second material is $M^1_aM^2_bO_x$;

(ii) the first material is $M^1O_x$, and the second material is $M^1_aM^2_bM^3_cO_x$;

(iii) the first material is $M^1_aM^2_bO_x$, and the second material is $M^1_aM^2_bM^3_cO_x$;

(iv) the first material is a first $M^1O_x$, and the second material is a second $M^1O_x$;

(v) the first material is a first $M^1_aM^2_bO_x$, and the second material is a second $M^1_aM^2_bO_x$; and (vi) the first material is a first $M^1_aM^2_bM^3_cO_x$, and the second material is a second $M^1_aM^2_bM^3_cO_x$; wherein $M^1$ is selected from the group consisting of Ce, Co, Cu, Fe, Ga, Nb, Ni, Pr, Ru, Sn, Ti, Tm, W, Yb, Zn, and Zr; $M^2$ and $M^3$ are each independently selected from the group consisting of Al, Ba, Bi, Ca, Cd, Ce, Co, Cr, Cu, Fe, Ga, Ge, In, K, La, Mg, Mn, Mo, Na, Nb, Ni, Pb, Pr, Rb, Ru, Sb, Sc, Si, Sn, Sr, Ta, Ti, Tm, V, W, Y, Yb, Zn, and Zr, but $M^2$ and $M^3$ are not the same in $M^1_aM^2_bM^3_cO_x$; a, b and c are each independently about 0.0005 to about 1; and and x is a number sufficient so that the oxygen present balances the charges of the other elements in the compound.

The sensor materials may optionally contain one or more additives to promote adhesion to a substrate, or that alter the conductance, resistance or selectivity of the sensor material. Examples of additives to promote adhesion are frits, which are finely ground glass, or finely ground inorganic minerals that are transformed into glass or enamel on heating. Illustrative frits include those designated as F2834, F3876, F2967, KH770, KH710 and KH375, available from DuPont iTechnologies. These may be used in amounts of up to 30 volume percent of the composition from which the sensor material is made. Examples of additives to alter the conductance, resistance or selectivity include Ag, Au or Pt as well as frits.

If desired, the sensor materials may also contain additives that, for example, catalyze the oxidation of a gas of interest or promote the selectivity for a particular analyte gas; or contain one or more dopants that convert an n semiconductor to a p semiconductor, or vice versa. These additives may be used in amounts of up to 30 weight percent of the composition from which the sensor material is made. Any frits or other additives used need not be uniformly or homogeneously distributed throughout the sensor material as fabricated, but may be localized on or near a particular surface thereof as desired. Each chemo/electro-active material may, if desired, be covered with a porous dielectric overlayer. A suitable overlayer is QM44 from DuPont iTechologies.

Any method of depositing the chemo/electro-active material to a substrate is suitable. One technique used for deposition is applying a semiconducting material on an alumina substrate on which electrodes are screen printed. The semiconducting material can be deposited on top of electrodes by hand painting semiconducting materials onto the substrate, nanopipetting materials into wells, thin film deposition, or thick film printing techniques. Most techniques are followed by a final firing to sinter the semiconducting materials.

Figure 2:
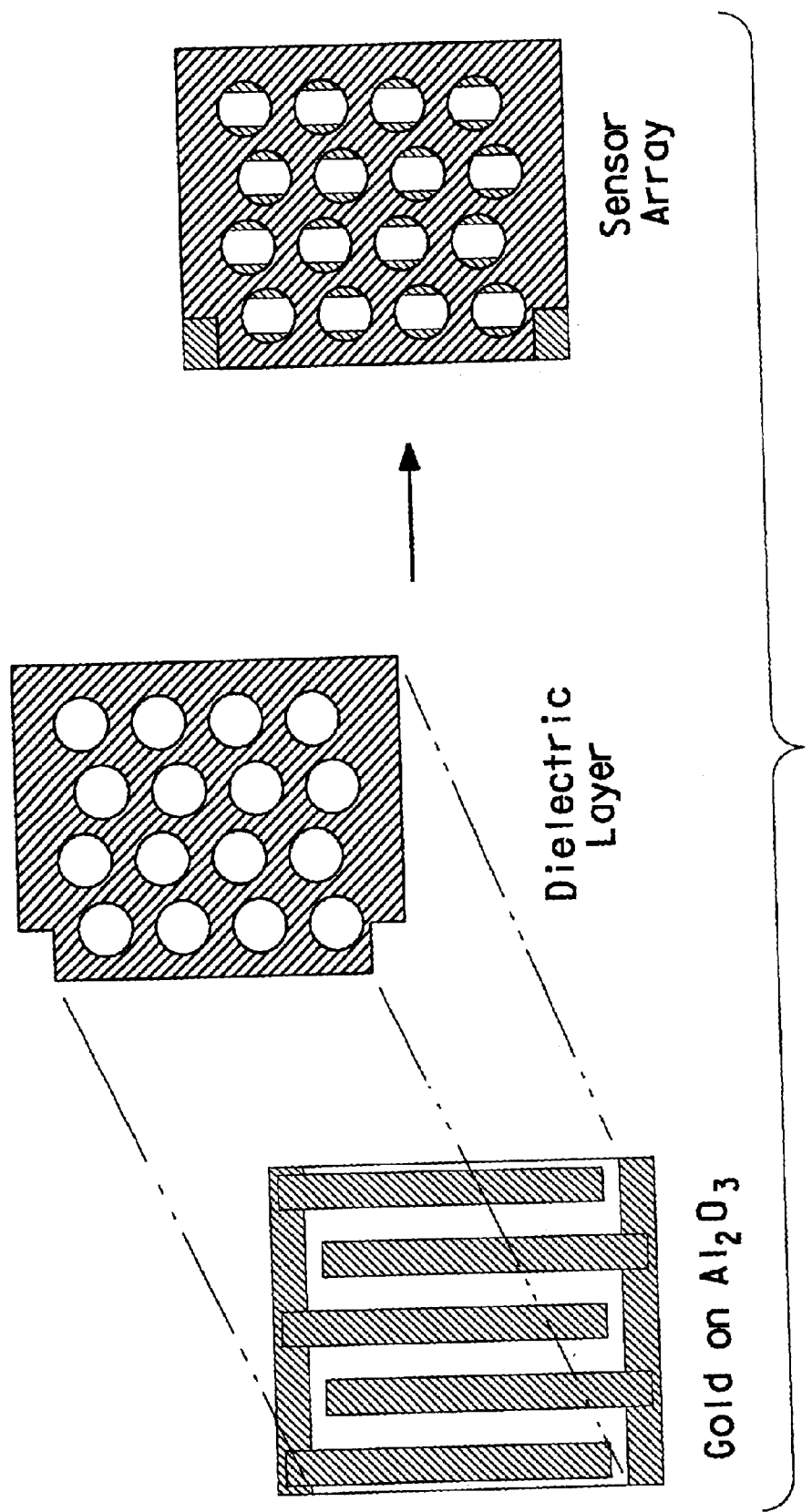
FIG. 2 is a schematic of the pattern of interdigitated electrodes overlaid with a dielectric overlayer, forming sixteen blank wells, in an array of chemo/electro-active materials.
Figure 3A:
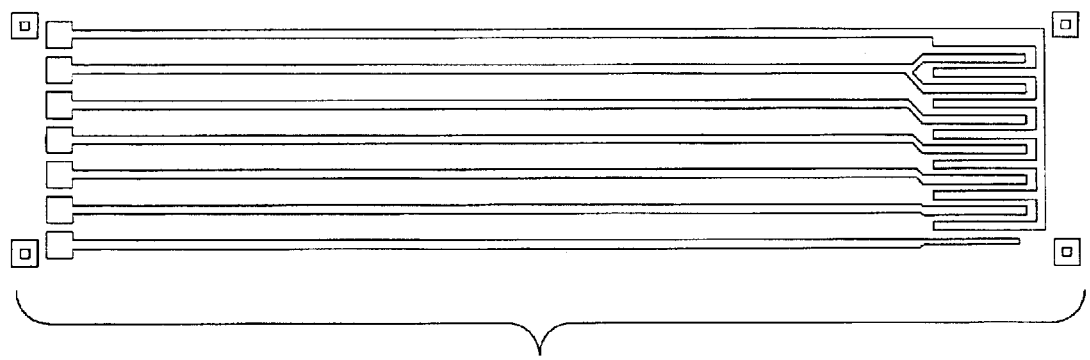
FIG. 3 depicts the electrode pattern, dielectric pattern, and sensor material pattern in an array of chemo/electro-active materials.
Figure 3B:
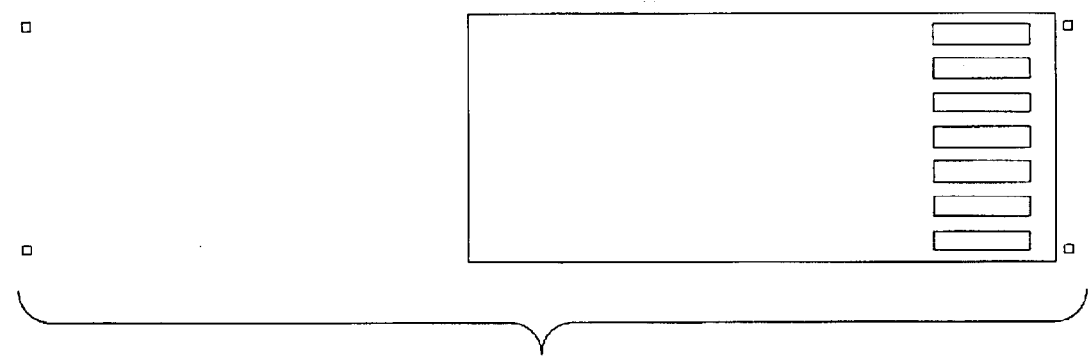
Figure 3C:
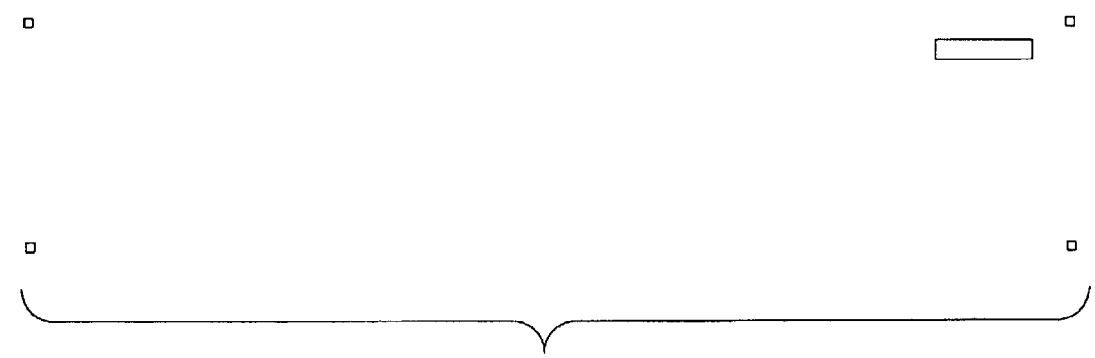

Techniques for screen-printing substrates with the electrodes and chemo/electro-active materials are illustrated in FIGS. 2–3. FIG. 2 depicts a method of using interdigitated electrodes overlaid with dielectric material, forming blank wells into which the chemo/electro-active materials can be deposited. FIG. 3 depicts an electrode screen pattern for an array of 6 materials which is printed on both sides of the substrate to provide for a 12-material array chip. Two of the electrodes are in parallel so it holds only 6 unique materials. Counting down from the top of the array shown in FIG. 3, the top two materials can only be accessed simultaneously by the split electrode with which they have shared contact. Below that is the screen pattern for the dielectric material, which is screen printed on top of the electrodes on both sides of the substrate to prevent the material from being fouled by contact with the gas mixture, such as a deposit of soot that could cause a short. Below that is the screen pattern for the actual sensor materials. This is printed in the holes in the dielectric on top of the electrodes. When more than one material is used in the array, the individual materials are printed one at a time.

An electrical response is determined for each chemo/electro-active material upon exposure of the array to a gas mixture, and means for determining the response include conductors interconnecting the sensor materials. The conductors are in turn connected to electrical input and output circuitry, including data acquisition and manipulation devices as appropriate to measure and record a response exhibited by a sensor material in the form of an electrical signal. The value of a response, such as a measurement related to resistance, may be indicated by the size of the signal. One or more signals may be generated by an array of sensors as to each analyte component in the mixture, whether the analyte is one or more individual gases and/or one or more subgroups of gases.

An electrical response is determined for each individual chemo/electro-active material separately from that of each of the other chemo/electro-active materials. This can be accomplished by accessing each chemo/electro-active material with an electric current sequentially, using a multiplexer to provide signals differentiated between one material and another in, for example, the time domain or frequency domain. It is consequently preferred that no chemo/electro-active material be joined in a series circuit with any other such material. One electrode, by which a current is passed to a chemo/electro-active material, can nevertheless be laid out to have contact with more than one material. An electrode may have contact with all, fewer than all, of the chemo/electro-active materials in an array. For example, if an array has 12 chemo/electro-active materials, an electrode may have contact with each member of a group of 2, 3, 4, 5 or 6 (or, optionally, more in each instance) of the chemo/electro-active materials. The electrode will preferably be laid out to permit an electrical current to be passed to each member of such group of chemo/electro-active materials sequentially.

A conductor such as a printed circuit may be used to connect a voltage source to a sensor material, and, when a voltage is applied across the sensor material, a corresponding current is created through the material. Although the voltage may be AC or DC, the magnitude of the voltage will typically be held constant. The resulting current is proportional to both the applied voltage and the resistance of the sensor material. A response of the material in the form of either the current, voltage or resistance may be determined, and means for doing so include commercial analog circuit components such as precision resistors, filtering capacitors and operational amplifiers (such as a OPA4340). As voltage, current and resistance is each a known function of the other two electrical properties, a known quantity for one property may be readily converted to that of another.

Resistance may be determined, for example, in connection with the digitization of an electrical response. Means for digitizing an electrical response include an analog to digital (A/D) converter, as known in the art, and may include, for example, electrical components and circuitry that involve the operation of a comparator. An electrical response in the form of a voltage signal, derived as described above as a result of applying a voltage across a sensor material, is used as an input to a comparator section (such as a LM339). The other input to the comparator is driven by a linear ramp produced by charging a capacitor using a constant current source configured from an operational amplifier (such as a LT1014) and an external transistor (such as a PN2007a). The ramp is controlled and monitored by a microcomputer (such as a T89C51CC01). A second comparator section is also driven by the ramp voltage, but is compared to a precise reference voltage. The microcomputer captures the length of time from the start of the ramp to the activation of the comparators to generate a signal based on the counted time.

The resistance of the sensor material is then calculated, or quantified as a value, by the microcomputer from the ratio of the time signal derived from the voltage output of the material to a time signal corresponding to a known look-up voltage and, ultimately, to the resistance that is a function of the look-up voltage. A microprocessor chip, such as a T89C51CC10, can be used for this function. The microprocessor chip may also serve as means for determining a change in the resistance of a sensor material by comparing a resistance, determined as above, to a previously determined value of the resistance.

Electrical properties such as impedance or capacitance may be determined, for example, by the use of circuitry components such as an impedance meter, a capacitance meter or inductance meter.

Means for digitizing the temperature of an array of chemo/electro-active materials can include, for example, components as described above that convert a signal representative of a physical property, state or condition of a temperature measuring device to a signal based on counted time.

In one embodiment, analysis of a multi-component gas mixture is complete upon the generation of an electrical response, such as resistance, in the manner described above. As a measurement of resistance exhibited by a sensor material upon exposure to a gas mixture is a function of the partial pressure within the mixture of one or more component gases, the measured resistance provides useful information about the composition of the gas mixture. The information may, for example, indicate the presence or absence within the mixture of a particular gas or subgroup of gases. In other embodiments, however, it may be preferred to manipulate, or further manipulate, an electrical response in the manner necessary to obtain information concerning the relative concentration within the mixture of one or more particular component gases or subgroups of gases, or to calculate the actual concentration within the mixture of one or more component gases or subgroups.

Means for obtaining information concerning the relative concentration within the mixture of one or more individual component gases and/or one or more subgroups of gases, or for detecting the presence of, or calculating the actual concentration of, one or more individual component gases and/or subgroups within the mixture, may include a modeling algorithm that incorporates either a PLS (Projection onto Latent Systems) model, a back-propagation neural network model, or a combination of the two, along with signal pre-processing and output post-processing. Signal pre-processing includes, but is not limited to, such operations as principle component analyses, simple linear transformations and scaling, logarithmic and natural logarithmic transformations, differences of raw signal values (e.g., resistances), and differences of logarithmic values. The algorithm contains a model whose parameters have been previously determined, and that empirically models the relationship between the pre-processed input signal and information related to the gas concentration of the species of interest. Output post-processing includes, but is not limited to, all of the operations listed above, as well as their inverse operations.

The model is constructed using equations in which constants, coefficients or other factors are derived from pre-determined values characteristic of a precisely measured electrical response of an individual sensor material to a particular individual gas or subgroup expected to be present as a component in the mixture to be analyzed. The equations may be constructed in any manner that takes temperature into account as a value separate and apart from the electrical responses exhibited by the sensor materials upon exposure to a gas mixture. Each individual sensor material in the array differs from each of the other sensors in its response to at least one of the component gases or subgroups in the mixture, and these different responses of each of the sensors is determined and used to construct the equations used in the model.

The analyte gas(es) contained in the mixture to which the chemo/electro-active material will be exposed can be a single gas, a subgroup of gases together, or one or more gases or subgroups mixed with an inert gas such as nitrogen. Particular gases of interest are donor and acceptor gases. These are gases that either donate electrons to the semiconducting material, such as carbon monoxide, $H_2S$ and hydrocarbons, or accept electrons from the semiconducting material, such as $O_2$, nitrogen oxides (commonly depicted as $NO_x$), and halogens. When exposed to a donor gas, an n-type semiconducting material will have a decrease in electrical resistance, increasing the current, and it, therefore, will show an increase in temperature due to $I^2R$ heating. When exposed to an acceptor gas, an n-type semiconducting material will have an increase in electrical resistance, decreasing the current, and therefore will show a decrease in temperature due to $I^2R$ heating. The opposite occurs in each instance with p-type semiconducting materials.

The geometry of a sensor material as fabricated in an array, including such characteristics as its thickness, selection of a compound or composition for use as the sensor, and the voltage applied across the array, can vary depending on the sensitivity required. The sensor materials are preferably connected in parallel in a circuit to which a voltage of about 1 to about 20, preferably about 1 to about 12, volts is applied across the sensor materials. When performing an analysis of a muti-component gas mixture, it is preferred that each chemo/electro-active sensor material in the array exhibit a different electrical response characteristic than each of the other chemo/electro-active materials in the array upon exposure to the mixture containing one or more analyte gases.

As noted, the types of electrical response characteristics that may be measured include AC impedance or resistance, capacitance, voltage, current or DC resistance. It is preferred to use resistance as the electric response characteristic of a sensor material that is measured to perform analysis of a gas mixture and/or a component therein. For example, a suitable sensor material may be that which, when at a temperature of about 400° C. or above, has a resistivity of at least about 1 ohm-cm, and preferably at least about 10 ohm-cm, and yet no more than about $10^6$ ohm-cm, preferably no more than about $10^5$ ohm-cm, and more preferably no more than about $10^4$ ohm-cm. Such a sensor material may also be characterized as that which exhibits, preferably at a temperature of about 400° C. or above, upon exposure to a gas mixture, a change in resistance of at least about 0.1 percent, and preferably at least about 1 percent, as compared to the resistance in the absence of exposure.

Regardless of the type of response characteristic that is measured for the purpose of analyzing a mixture and/or a gaseous component of interest therein, it is desirable that a sensor material be utilized for which a quantified value of that response characteristic is stable over an extended period of time. When the sensor material is exposed to a mixture containing the analyte, the concentration of the analyte being a function of the composition of the particular gas mixture in which it is contained, the value of the response of the sensor material will preferably remain constant or vary to only a small extent during exposure to the mixture over an extended period of time at a constant temperature. For example, the value of the response, if it varies, will vary by no more than about twenty percent, preferably no more than about ten percent, more preferably no more than about five percent, and most preferably no more than about one percent over a period of at least about 1 minute, or preferably a period of hours such as at least about 1 hour, preferably at least about 10 hours, more preferably at least about 100 hours, and most preferably at least about 1000 hours. One of the advantages of the types of sensor materials described above is that they are characterized by this kind of stability of response.

In applications in which the gas mixture is above about 400° C., the temperature of the sensor materials and the array may be determined substantially only, and preferably is determined solely, by the temperature of the gas mixture in which a gaseous analyst is contained. This is typically a variable temperature. When higher-temperature gases are being anaylzyed, it may be desirable to provide a heater with the array to bring the sensor materials quickly to a minimum temperature. Once the analysis has begun, however, the heater (if used) is typically switched off, and no method is provided to maintain the sensor materials at a preselected temperature. The temperature of the sensor materials thus rises or falls to the same extent that the temperature of the surrounding environment does. The temperature of the surrounding environment, and thus the sensors and the array, is typically determined by (or results from) substantially only the temperature of the gas mixture to which the array is exposed.

In applications in which the gas mixture is below about 400° C., it may be preferred to maintain the sensor materials and the array at a preselected temperature of about 400° C. or above. This preselected temperature may be substantially constant, or preferably is constant. The preselected temperature may also be about 500° C. or above, about 600° C. or above, or about 700° C. or above. This may be conveniently done with a heater incorporated with the array, in a manner as known in the art. The temperature of the gas mixture may also be below about 300° C., below about 200° C., or below about 100° C.

A change of temperature in the array may be indicated by a change in the quantified value of an electrical response characteristic, resistance for example, of a sensor material. At a constant partial pressure in the mixture of a gas of interest, the value of an electrical response characteristic of a sensor material may vary with a change in temperature of the array, and thus the material. This change in the value of an electrical response characteristic may be measured for the purpose of determining or measuring the extent of change of, and thus a value for, temperature. It is not required, but is preferred, that this measurement of temperature be made independently of information related to the compositional content of a gas mixture. This can be done by not using sensors that provide compositional information for the additional purpose of determining temperature, and, optionally, by connecting the temperature measuring device in parallel circuitry with the sensor materials, rather than in series. Means for measuring temperature include a thermocouple or a pyrometer incoporated with an array of sensors. If the temperature determining device is a thermistor, which is typically a material that is not responsive to an analyte gas, the thermistor is preferably made from a different material than the material from which any of the gas sensors is made. Regardless of the method by which temperature or change in temperature is determined, a temperature value or a quantified change in temperature is a desirable input, preferably in digitized form, from which an analysis of a mixture of gases and/or a component therein may be performed.

In the method and apparatus of this invention, unlike various prior-art technologies, there is no need to separate the component gases of a mixture for purposes of performing an analysis, such as by a membrane or electrolytic cell. There is also no need when performing an analysis by means of this invention to employ a reference gas, such as for the purpose of bringing a response or analytical results back to a base line value. With the exception of preliminary testing, during which a standardized response value to be assigned to the exposure of each individual sensor material to each individual analyte gas is determined, the sensor materials are exposed only to the mixture in which an analyte gas and/or subgroup is contained. The sensor materials are not exposed to any other gas to obtain response values for comparison to those obtained from exposure to the mixture containing an analyte. The analysis of the mixture is therefore performed only from the electrical responses obtained upon exposure of the chemo/electro-active materials to the mixture containing the analyte. No information about an analyte gas and/or subgroup is inferred by exposure of the sensor materials to any gas other than the analyte itself as contained within the mixture.

This invention therefore provides methods and apparatus for directly sensing the presence and/or concentration of one or more gases in an multi-component gas system, comprising an array of at least two chemo/electro-active materials chosen to detect the gases in a multi-component gas stream. The multi-component gas system can be at essentially any temperature that is not so low or so high that the sensor materials are degraded or the sensor apparatus otherwise malfunctions. In one embodiment, the gas system may be at a lower temperature such as room temperature (about 25° C.) or elsewhere in the range of about 0° C. to less than about 100° C., whereas in another embodiment the gas mixture may at a higher temperature such as in the range of about 400° C. to about 1000° C.

The invention is applicable to gas mixtures that may be at higher temperatures—gases, for example, as found in combustion streams such as the exhaust or emission of an automobile, diesel engine or home heating system. The invention is also applicable, however, to gas mixtures derived from other sources, such as in manufacturing processes, waste streams, and environmental monitoring; or in systems in which odor detection is important and/or that are at lower temperature, such as in the medical, agricultural or food and beverage industries. An array of chemo/electro-active materials could be used, for example, to supplement the results of, or calibrate, a gas chromatograph. The gas mixture may therefore have a temperature that is about 100° C. or more, about 200° C. or more, about 300° C. or more, about 400° C. or more, about 500° C. or more, about 600° C. or more, about 700° C. or more, or about 800° C. or more, and yet is less than about 1000° C., is less than about 900° C., is less than about 800° C., is less than about 700° C., is less than about 600° C., is less than about 500° C., is less than about 400° C., is less than about 300° C., is less than about 200° C., or is less than about 100° C.

This invention further provides means to determine, measure and record responses exhibited by each of the chemo/electro-active materials present in an array upon exposure to a gas mixture. For example, any means that will determine, measure and record changes in electrical properties can be used. This may, for example, be a device that is capable of measuring the change in AC impedance of the materials in response to the concentration of adsorbed gas molecules at their surfaces. Other means for determining electrical properties can be suitable devices used to measure, for example, capacitance, voltage, current or DC resistance. Alternatively a change in temperature of the sensing material may be measured and recorded. The chemical sensing method and apparatus may further provide means to measure or analyze a mixture and/or the detected gases such that the presence of the gases are identified and their concentrations are measured. These means can includeinstrumentation or equipment that is capable, for example, of performing chemometrics, neural networks or other pattern recognition techniques. The chemical sensor apparatus will further comprise a housing for the array of chemo/electro-active materials, the means for detecting, and means for analyzing.

This invention also provides a chemical sensor for directly sensing the presence and/or concentration of one or more gases in a multi-component gas system, including a substrate, an array of at least two chemo/electro-active materials chosen to detect one or more predetermined gases in a multi-component gas stream, and a means to detect changes in electrical properties in each of the chemo/electro-active materials present upon exposure to the gas system.

The array of sensor materials should be able to detect an analyte of interest despite competing reactions caused by the presence of the several other components of a multi-component mixture. For this purpose, this invention uses an array of multiple sensor materials, as described herein, each of which has a different sensitivity for at least one of the gas components of the mixture to be detected. A sensor that has the needed sensitivity, and that can operate to generate the types of analytical measurements and results described above, is obtained by selection of appropriate compositions of materials from which the sensor is made. Various suitable compositions of materials for this purpose are described above. The number of sensors in the array is typically greater than or equal to the number of individual gas components to be analyzed in the mixture.

The gas mixture to be analyzed may be emitted by a process, or may be a product of a chemical reaction that is transmitted to a device. In such instance, the apparatus of this inveniton may further include means for utilizing the electrical response of an array, and optionally a temperature measurement, for the purpose of controlling the process or the device.

Means for utilizing an electrical response of a sensor material, and optionally a temperature measurement, for controlling a process or device include a decision making routine to control, for example, the chemical reaction of combustion that occurs in an internal combustion engine, or to control the engine itself, or components or equipment associated therewith.

Combustion is a process in which the chemical reaction of the oxidation of a hydrocarbon fuel occurs in the cylinder of an engine. An engine is a device to which a result of that chemical reaction is transmitted, the result being the force generated by the combustion reaction to the work necessary to move the piston in the cylinder. Another example of a process that emits a multi-component mixture of gases is the chemical reaction that occurs in a fuel cell, and other examples of a device to which a product of a chemical reaction is transmitted is a boiler, such as used in a furnace or for power generation, or a scrubber in a stack to which waste gases are transmitted for pollution abatement treatment.

In the case of an engine, to control the process of combustion or the operation of the engine itself, a microcomputer (such as a T89C51CC01) performs a multitude of decision-making routines about various parameters of the process of combustion or about operating characteristics of the engine. The microcomputer gathers information about the compositional content of the engine exhaust, and does so by obtaining the responses of an array of chemo/electro-active materials that have been exposed to the stream of exhaust, and optionally obtains a temperature measurement. The information is temporarily stored in a random access memory, and the microcomputer then applies one or more decision-making routines to the information.

A decision-making routine utilizes one or more algorithms and/or mathematical operations to manipulate the acquired information to generate a decision in the form of a value that is equivalent to a desired state or condition that should be possessed by a particular parameter of the process, or by an operating characteristic of the device. Based on the result of a decision-making routine, instructions are given by or are controlled by the microcomputer that cause an adjustment in the state or condition of a parameter of the process or an operating characteristic of the device. In the case of the process embodied by the chemical reaction of combustion, the process can be controlled by adjusting a parameter of the reaction, such as the relative amount of the reactants fed thereto. The flow of fuel or air to the cylinder, for example, can be increased or decreased. In the case of the engine itself, being a device to which a result of the reaction of combustion is transmitted, control can be accomplished by adjusting an operating characteristic of the engine such as torque or engine speed.

An internal combustion engine and the associated components and equipment, controlled by the methods and apparatus of this invention, can be used for many different purposes including, for example, in any type of vehicle for transportation or recreation such as a car, truck, bus, locomotive, aircraft, spacecraft, boat, jet ski, all-terrain vehicle or snowmobile; or in equipment for construction, maintenance or industrial operations such as pumps, lifts, hoists, cranes, generators, or equipment for demolition, earth moving, digging, drilling, mining or groundskeeping.

The following non-limiting examples are meant to illustrate the invention but are not intended to limit it in any way. In the examples provided below, "chip" is used to describe an alumina substrate comprising an electrode and sensing material, and dielectric, if a dielectric is used. The notation "X% A:MO" means that another inorganic compound (A) has been added at the specified concentration (X% on an atomic basis) to the metal oxide (MO). The term "frit" is used to describe a mixture of inorganic compounds that usually form a glass at some temperature.

EXAMPLES

Described below are exemplary techniques that may be used to prepare sensor materials, and to measure signals using infrared (IR) thermographic and AC impedance techniques.

IR Thermographic Samples and Measurements

The change in impedance of a sensor material when exposed to a gas or gas mixture may be determined by measuring the change in temperature of the material sample by a technique such as infrared thermographic imaging.

A. Array Chip Fabrication

A blank array chip was made by screen printing an interdigitated electrode pattern, shown in FIG. 2, onto an alumina substrate (obtained from Coors Tek, 96% alumina, 1"×0.75"×0.025"). A semi-automatic screen printer (ETP Electro-dial, Series L-400) was used. The electrode paste is available from DuPont iTechnologies, product #5715. The electrode screen that was used (obtained from Microcircuit Engineering Corporation) had an emulsion thickness of 0.5 mil. After screen printing, the parts were dried in a convection oven at 120° C. for 10 minutes and then fired. Firing was done in air using a 10 zone belt Lindberg furnace with a cycle time of 30 minutes and a peak temperature of 850° C. for 10 minutes. After the electrodes were fired onto the substrate a dielectric (DuPont iTechnologies, product #5704) pattern, shown in FIG. 2, was screen printed over the electrodes with a screen (Microcircuit Engineering Corporation), having an emulsion thickness of 0.9 mil. The parts were then dried at 120° C. for 10 minutes and fired using the same firing cycle as described above.

B. Semiconducting Metal Oxide Preparation and Application on the Array Chip

Approximately 175 mg of the semiconducting metal oxide powder or the mixture of a semiconducting metal oxide with a suitable glass frit (DuPont iTechnologies product #F2889 or F3876) or the mixture of the semiconducting metal oxide powder with other inorganic compounds was weighed out on to a glass slide with approximately 75 mg of a suitable medium (DuPont iTechnologies product #M2619) and 1 mg of a suitable surfactant (DuPont iTechnologies product #R0546). The medium and surfactant were mixed together and the metal oxide powder or mixture was added to the medium and surfactant gradually to ensure wetting. If needed, a suitable solvent (DuPont iTechnologies product #R4553) was added at this time to reduce the viscosity. The paste was then transferred to an agate mortar and pestle for more thorough mixing. Using a finely pointed wooden applicator, a very small amount of paste was then placed into one of the wells of the array chip. This procedure was repeated with each of the metal oxide powders or mixtures until all of the wells on the array chip were filled. Once the wells on the array chip were filled with pastes, the array chip was allowed to sit in a closed chamber with a low flow of $N_2$ gas passing over the chip. The array chip was then dried at 120° C. for 10 minutes. Firing was done in air using a Fisher programmable box furnace with a 1° C./minute ramp rate up to 650° C., where it was held at temperature for 30 minutes. The cooling rate was 5° C./minute to room temperature.

C. Wiring of the Array Chip

Lead wires were fabricated using approximately 1.5" of 0.005" platinum wire. One end of the wire was bare and the other end was connected to a female RS232 connector. The bare end of a platinum lead wire was attached to one of the open conductor pads on the array chip using a conducting paste (Pelco product #16023). A second lead wire was attached the same way to the other open conductor pad on the array chip. The chip was then allowed to dry for at least 4 hours at 120° C.

D. IR Thermographic Measurements

The test chamber comprised a 2.75" cube containing input and output valves for gas flow, a 1" MgF window, two thermocouple feedthroughs and two electrical feedthroughs. The electrical feedthroughs provided connections to the sample heater (Advanced Ceramics, Boralectric heater # HT-42) and the voltage/current measuring unit (Keithley Instruments model #236). The gas flows were regulated using a multi-gas controller (MKS model #647B). The sample heater was controlled using a unit from Hampton Controls (70VAC/700W phase angle). The infrared camera (Inframetrics PM390) was focused on the front surface of the array chip using a 100 $\mu$m close-up lens during the measurements.

Before the measurements were made the sample was placed inside the test chamber on top of the sample heater. The female pins on the lead wires connected to the array chip were then connected to the electrical feedthrough connected to the voltage/current measuring unit. The chamber was closed and placed in the visual path of the IR camera. Gas (100 sccm $N_2$, 25 sccm $O_2$) was then allowed to flow into the chamber during heating of the sample. Next, the sample was heated (approximately 10° C./minute) to the desired temperature and equilibrated before the voltage/current measuring unit was turned on and a voltage applied. The voltage was typically adjusted to allow a current flow of between 10–20 mA through the array.

IR thermographic images of the array of materials were taken 20 minutes after each change in the flows of the following gases: $N_2$, $O_2$, and gas mixtures as follows: 1% CO/99% $N_2$, 1% $NO_2$/99% $N_2$ and 1% $C_4H_{10}$/99% $N_2$. Unless otherwise noted, the content of all gas mixtures described below is stated in percent by volume. The temperatures of the materials in 2% $O_2$/98% $N_2$ were subtracted from their temperatures in the other gas mixtures to determine the temperature signals in the examples. ThermMonitor 95 Pro, version 1.61 (Thermoteknix Systems, Ltd.) was used to do the temperature subtractions. When exposed to a donor gas, n-type semiconducting materials will have a decrease in resistivity, increasing the current and therefore, will show an increase in temperature due to $I^2R$ heating. When exposed to an acceptor gas, n-type semiconducting materials will have an increase in resistivity, decreasing the current and therefore will show a decrease in temperature due to $I^2R$ heating. The opposite occurs with p-type semiconducting materials.

AC Impedance Samples and Measurements

A. Semiconducting Metal Oxide Paste Preparation

Approximately 2–3 grams of the semiconducting metal oxide powder or the mixture of a semiconducting metal oxide with a suitable glass frit (DuPont iTechnologies product #F2889 or F3876) or the mixture of the semiconducting metal oxide with other inorganic compounds was weighed out with an amount of a suitable medium (DuPont iTechnologies product #M2619) sufficient to provide approximately 40–70 weight % solids. These materials were then transferred to a muller (Hoover automatic muller, model #M5) where they were mixed together using a spatula until no dry powder was left. If needed, a suitable surfactant, such as DuPont iTechnologies product #R0546, was added to reduce the viscosity. Further mixing was done using the muller with 500 grams of weight for approximately 6 passes at 25 revolutions per pass. The finished pastes were then transferred to containers until needed.

B. Single Sensor Fabrication

Some of the sensing chips were prepared using a single material and not arrays of sensing materials. The single sensing sample chips were made by screen printing an interdigitated electrode pattern with electrodes, which are 0.4" long and have a 0.008" spacing onto an alumina substrate (Coors Tek, 96% alumina, 1"×1"×0.025"). A semi-automatic screen printer (ETP Electro-dial, Series L-400) was used. The electrode paste (product #5715) is available from DuPont iTechnologies. The electrode screen (Microcircuit Engineering Corporation) had an emulsion thickness of 0.5 mil. After printing, the parts were dried in a convection oven at 120° C. for 10 minutes and then fired. Firing was done using a 10 zone belt furnace (Lindberg) with a cycle time of 30 minutes and a peak temperature of 850° C. for 10 minutes. The sensor material was then screen printed on the substrate using a screen (Microcircuit Engineering Corporation) with an open area 0.5"×0.5". This screen had an emulsion thickness of 1.0 mil. After the sensor material was printed the part was dried in a convection oven at 120° C. for 10 minutes. At this point the part was fired in air to 850° C. for 10–45 minutes using a Lindberg tube furnace.

C. Sensor Array Fabrication

A variety of electrode and sensor configurations can be used to acquire the AC impedance data of the sensor array. Described immediately below is the fabrication of a 12-material array.

The sensor array chip was made by screen printing an electrode pattern (FIG. 3) onto an alumina substrate (Coors Tek, 96% alumina, 2.5"×0.75"×0.040"). A semi-automatic screen printer (ETP Electro-dial, Series L-400) was used. The electrode paste (product #4597) is available from DuPont iTechnologies. The electrode screen (Microcircuit Engineering Corporation) had an emulsion thickness of 0.4 mil. Note in FIG. 3 that two of the sensor pads are in parallel, so that only six unique sensor material measurements can be made from this electrode configuration. After printing, the parts were dried in a convection oven at 130° C. for 10 minutes and then fired. Firing was done in air using a 10 zone belt furnace (Lindberg) with a cycle time of 30 minutes and a peak temperature of 850° C. for 10 minutes. After the electrodes were fired onto the substrate a dielectric (DuPont iTechnologies, product #QM44) pattern, shown in FIG. 3, was screen printed over the electrodes with a screen (Microcircuit Engineering Corporation), having an emulsion thickness of 1.0 mil. The parts were then dried at 130° C. for 10 minutes and fired using the same firing cycle as described above. At this point, each sensor material was screen printed on the substrate into the wells of the dielectric using the screen (Microcircuit Engineering Corporation), shown in FIG. 3. This screen had an emulsion thickness of 1.0 mil. After each sensor material was printed the part was dried in a convection oven at 130° C. for 10 minutes. After all of the sensor materials (6) were applied to this side of the sensor, the part was fired using the same firing cycle as described above. After this firing step, the above printing, drying and firing steps were repeated on the back side of the substrate to add 6 more sensor materials to the array chip.

D. AC Impedance Measurements

For single sensor material samples, a 1.2" platinum wire was connected to each of the electrodes on the samples with stainless steel screws. The ends of the platinum wires were then connected to 0.127" diameter inconel wires that run to the exterior of the test chamber. The entire lengths of the inconel wires were encased in aluminum oxide and grounded inconel tubing to eliminate interference from electromagnetic fields present in the furnace. The inconel tubes were welded into a stainless steel flange that was mounted on the end of a closed-one-end fused quartz reactor that is 4" in diameter and 24" long. The quartz reactor was wrapped with grounded stainless steel screen also to eliminate electromagnetic interference from the furnace. The entire chamber assembly was placed in the cavity of a hinged Lindberg tube furnace and the furnace was closed.

The samples were connected to the dielectric interface (Solartron 1296) and frequency response analyzer (Solartron 1260) using ten pairs of coaxial cables (one pair per sample) which ran from the inconel wires on the furnace exterior to a switch (Keithley 7001 containing two Keithley 7062 high frequency cards) and one pair of coaxial cables from the switch to the interface and analyzer. The switch, dielectric interface and frequency analyzer were all computer controlled.

The gas flows into the quartz chamber were regulated using a computer controlled system comprised of 4 independent flowmeters (MKS product #1179) and multi gas controller (MKS product #647B). The temperature of the furnace was determined using a computer controlled fuzzy logic controller (Fuji PYX).

After the samples were loaded into the furnace, the quartz reactor was purged with a synthetic air mixture during heating of the furnace. After the furnace was equilibrated at the measurement temperature, the gas concentrations ($N_2$, $O_2$, 1% CO/99% $N_2$, and 1% $NO_2$/99% $N_2$ were set to the desired values and sufficient time was allowed for the equilibration of the atmosphere in the reactor. At this point the AC impedance measurements (1 Hz to 1 MHz) from each sample were measured sequentially. Then the gas concentrations were typically set to a new value, the atmosphere was equilibrated, and another round of measurements were made. The procedure was repeated until the samples were measured in all of the desired atmospheres at a particular temperature. At this point the temperature was changed and the process repeated. After all of the measurements had been made the furnace was cooled to room temperature and the samples removed.

For the sensor array chips, a measurement system similar to that described above can be used. The only difference is that the platinum wires, which are connected to the inconel wires in the furnace, must be connected to the electrode pads on the array chip using a conducting paste (Pelco product #16023). The number of connections from the sample to the switch depends on the number of sensors on the array.

Example 1

This example shows the change in the electrical properties of 20 metal oxide semiconducting materials in the presence of 4 combustion gas compositions at 450° C. The signals listed in Table 1 below are from the infrared thermographic technique described above. The signals represent differences in temperature (° C.) of the materials when exposed to one of the 4 gas compositions shown relative to that in a comparison gas which is 2% $O_2$/98% $N_2$ and reflect the change in the electrical resistance of the semiconducting materials. All of the signals were generated with 10 V across the materials, unless otherwise specified. Blank spaces indicate that there was no detectable signal when that gas composition was contacted with that material. Unless otherwise specified, the gases were measured at 2000 ppm in $N_2$.

TABLE 1

| Change in temperature in ° C. | | | | | | | | | | | | |
|---|---|---|---|---|---|---|---|---|---|---|---|---|
| | ZnO | $SnO_2$ | $NiFe_2O_4$ | $WO_3$ | 1% $Nb:TiO_2$ | $Pr_6O_{11}$ | $SrNb_2O_6$ | NiO | CuO | $Cu_2O$ | $MnTiO_3$ | $BaCuO_{2.5}$ |
| $NO_2$ in $N_2$ | −38.1 | −35.4 | −27.4 | −16.4 | −2.7 | −5.6 | −2.8 | 5.5 | 8.2 | 8.2 | 5.6 | 6.6 |
| $NO_2$ in 2% $O_2$/98% $N_2$ | −35.2 | −32.5 | −13.7 | −13.5 | −2.7 | — | — | 5.5 | 5.6 | 5.5 | — | 2.6 |
| CO in $N_2$ | 27.2 | 8.2 | 14 | 13.7 | — | — | 8.3 | — | −5.5 | −13.8 | — | −2.7 |
| $N_2$ ref. | 16.9 | 9.6 | 11.2 | 5.6 | 12.4 | — | — | −2.8 | −5.6 | −2.8 | — | −2.7 |
| | | $AlVO_4$ | $CuMnFeO_4$ | $LaFeO_3$ | $CuGaO_2$ | $CuFe_2O_4$ | $Zn_4TiO_6$ | $La_2CuO_4$ | $SrCu_2O_2$ | | | |
| $NO_2$ in $N_2$ | | — | — | — | −2.8 | −5.5 | −5.7 | 4.2 | — | | | |
| $NO_2$ in 2% $O_2$/98% $N_2$ | | −2.7 | 2.6 | — | — | −2.5 | — | — | 2.6 | | | |
| CO in $N_2$ | | 11.3 | — | −2.8 | — | — | 7.3 | — | — | | | |
| $N_2$ ref. | | 8.3 | — | — | — | — | — | — | — | | | |

The following measurements were done with other than 10 V. $Pr_6O_{11}$ was measured using 1 V; $BaCuO_{2.5}$, $CuMnFeO_4$, $CuGaO_2$ and $CuFe_2O_4$ were measured using 16 V; $Zn_4TiO_6$ was measured using 20 V; $LaCuO_4$ and $SrCu_2O_2$ were measured using 12 V.

Example 2

This example shows the change in the electrical properties of 8 metal oxide semiconducting materials in the presence of 5 combustion gas compositions at 450° C. The signals listed in Table 2 below are from the infrared thermographic technique. The signals are differences in temperature (°C.) of the semiconducting materials when exposed to the gas compositions shown relative to that in a comparison gas which is 2% $O_2$/98% $N_2$. All of the signals were generated with 10 V across the semiconducting materials, unless otherwise specified. Blank spaces indicate that there was no detectable signal when that gas composition was contacted with that material. Unless otherwise specified, the gases were measured at 2000 ppm in $N_2$.

TABLE 2

| | Change in temperature in ° C. | | | | | | | |
|---|---|---|---|---|---|---|---|---|
| | ZnO | $SnO_2$ | $WO_3$ | $SrNb_2O_6$ | NiO | CuO | $Cu_2O$ | $AlVO_4$ |
| $NO_2$ in $N_2$ | −38.1 | −35.4 | −16.4 | −2.8 | 5.5 | 8.2 | 8.2 | — |

TABLE 2-continued

| | Change in temperature in ° C. | | | | | | | |
|---|---|---|---|---|---|---|---|---|
| | ZnO | $SnO_2$ | $WO_3$ | $SrNb_2O_6$ | NiO | CuO | $Cu_2O$ | $AlVO_4$ |
| $NO_2$ in 2% $O_2$/98% $N_2$ | −35.2 | −32.5 | −13.5 | — | 5.5 | 5.6 | 5.5 | −2.7 |
| CO in $N_2$ | 27.2 | 8.2 | 13.7 | 8.3 | | −5.5 | −13.8 | 11.3 |
| $N_2$ ref. | 16.9 | 9.6 | 5.6 | — | −2.8 | −5.6 | −2.8 | 8.3 |
| 1% $C_4H_{10}$/99% $N_2$ | 38 | 28 | 22 | — | −6 | −7 | −11 | 11 |

Example 3

This example shows the change in the electrical properties of 26 metal oxide semiconducting materials in the presence of 4 combustion gas compositions at 600° C. The signals listed in Table 3 immediately below were obtained using an infrared thermographic technique. The signals are measurements of the differences in temperature (° C.) of the materials when exposed to the gas compositions shown relative to that in a comparison gas which is 2% $O_2$/98% $N_2$. All of the signals were generated with 10 V across the materials, unless otherwise specified. Blank spaces indicate that there was no detectable signal when that gas composition was contacted with that material. Unless otherwise specified, the gases were measured at 2000 ppm in $N_2$.

TABLE 3

| | Change in temperature in ° C. | | | | | | | | | | | | | |
|---|---|---|---|---|---|---|---|---|---|---|---|---|---|---|
| | ZnO | $SnO_2$ | $NiFe_2O_4$ | 1% $Nb:TiO_2$ | $WO_3$ | $FeTiO_3$ | $SrTiO_3$ | NiO | $AlVO_4$ | CuO | $Cu_2O$ | $LaFeO_3$ | $BaCuO_{2.5}$ | $Fe_2O_3$ |
| $NO_2$ in $N_2$ | −54.4 | −48.3 | −36.3 | −24.2 | −18.1 | −6.1 | 3 | 6 | — | — | — | — | — | — |
| $NO_2$ in 2% $O_2$/98% $N_2$ | −48.3 | −48.3 | −30.2 | −12.1 | −18.1 | −6.1 | 6 | 6 | −6.1 | 6 | 6 | — | — | — |
| CO in $N_2$ | 28.5 | 18.1 | 18.5 | 42.3 | 24.1 | — | — | −6 | 18.1 | −6 | −12.1 | −3 | −6 | 72.5 |
| $N_2$ | 30.2 | 24.1 | 15.1 | 24.1 | 6 | 3 | — | −9.1 | 18.1 | −3 | — | — | −6 | — |

| | $SrNb_2O_6$ | ZnO + 2.5% F2889 | ZnO + 10% F3876 | $SnO_2$ + 5% F2889 | $WO_3$ + 10% F3876 | $CuFe_2O_4$ | $Zn_4TiO_6$ | $ZnTiO_3$ | $Tm_2O_3$ | $Yb_2O_3$ | $Fe:ZrO_2$ | $MnCrO_3$ |
|---|---|---|---|---|---|---|---|---|---|---|---|---|
| $NO_2$ in $N_2$ | — | −24 | −42 | −6 | −15 | −6 | −12 | −6 | −6 | −6 | −6 | — |
| $NO_2$ in 2% $O_2$/98% $N_2$ | — | −18 | −24 | −6 | −18 | −6 | — | — | — | — | — | — |
| CO in $N_2$ | 28.5 | 18 | 12 | 24 | 6 | — | 6 | — | — | — | 6 | 24 |
| $N_2$ | 18.1 | 21 | 27 | 9 | 18 | — | 6 | — | — | — | — | — |

All of the measurements were obtained using 10 V, except that $BaCuO_{2.5}$ was measured with 4 V; $Fe_2O_3$ was measured with 1 V; ZnO+2.5% F2889, ZnO+10% F3876, $SnO_2$+5% F2889, $Tm_2O_3$, $Yb_2O_3$, $Fe:ZrO_2$ and $MnCrO_3$ were measured with 5 V; $WO_3$+10% F3876 was measured with 2 V; $CuFe_2O_4$ was measured with 6 V; and $Zn_4TiO_6$ and $ZnTiO_3$ were measured using 20 V.

Example 4

This example illustrates that a set of 4 metal oxide materials of Example 3 could be used to differentiate the 4 gas compositions shown at 600° C. using the IR thermographic signals. The results are shown in Table 4 below. The signals are measurements of the differences in temperature (° C.) of the materials when exposed to the gases shown relative to that in a comparison gas which is 2% $O_2$/98% $N_2$. All of the signals were generated with 10 V across the materials, unless otherwise specified. Blank spaces indicate that there was no detectable signal when that gas composition was contacted with that material. Unless otherwise specified, the gases were measured at 2000 ppm in $N_2$.

TABLE 4

| | Change in temperature in ° C. | | | |
|---|---|---|---|---|
| | $SrTiO_3$ | $Cu_2O$ | $Fe_2O_3$ | $SrNb_2O_6$ |
| $NO_2$ in $N_2$ | 3 | — | — | — |
| $NO_2$ in 2% $O_2$/98% $N_2$ | 6 | 6 | — | — |
| CO in $N_2$ | — | −12.1 | 72.5 | 28.5 |
| $N_2$ | — | — | — | 18.1 |

Example 5

This example demonstrates that this second set of 4 metal oxide materials of Example 3 could be used to differentiate the 4 gas compositions shown at 600° C. using the IR thermographic signals. The results are shown in Table 5 below. The signals are measurements of the differences in temperature (° C.) of the materials when exposed to the gases shown relative to that in a comparison gas which is 2% $O_2$/98% $N_2$. All of the signals were generated with 10 V across the materials, unless otherwise specified. Blank spaces indicate that there was no detectable signal when that gas composition was contacted with that material. Unless otherwise specified, the gases were measured at 2000 ppm in $N_2$.

TABLE 5

| | Change in temperature in ° C. | | | |
|---|---|---|---|---|
| | ZnO | $AlVO_4$ | $LaFeO_3$ | $BaCuO_{2.5}$ |
| $NO_2$ in $N_2$ | −54.4 | — | — | — |
| $NO_2$ in 2% $O_2$/98% $N_2$ | −48.3 | −6.1 | — | — |
| CO in $N_2$ | 28.5 | 18.1 | −3 | −6 |
| $N_2$ | 30.2 | 18.1 | — | −6 |

Comparative Example A

This comparative example demonstrates that this set of 6 materials of Example 3 can not be used to differentiate the 2 gas compositions at 600° C. using the IR thermographic signals, and illustrates the importance of the proper selection of materials. The results are shown in Table 5A below. The signals are measurements of the differences in temperature (° C.) of the materials when exposed to the gas compositions shown relative to that in a comparison gas which is 2% $O_2$/98% $N_2$. All of the signals were generated with 10 V across the materials, unless otherwise specified. Blank spaces indicate that there was no detectable signal when that gas composition was contacted with that material. Unless otherwise specified, the gases were measured at 2000 ppm in $N_2$.

TABLE 5a

| | Change in temperature in ° C. | | | | | |
|---|---|---|---|---|---|---|
| | $SnO_2$ | $WO_3$ | $FeTiO_3$ | NiO | $SnO_2$ + 5% F2889 | $CuFe_2O_4$ |
| $NO_2$ in $N_2$ | −48.3 | −18.1 | −6.1 | 6 | −6 | −6 |
| $NO_2$ in 2% $O_2$/98% $N_2$ | −48.3 | −18.1 | −6.1 | 6 | −6 | −6 |

Comparative Example B

This comparative example demonstrates that this set of 3 materials can not be used to differentiate the 2 gas compositions at 600° C. using the IR thermographic signals, and illustrates the importance of the proper selection of materials. The results are shown in Table 5B below. The signals are measurements of the differences in temperature (° C.) of the materials when exposed to the gas compositions shown relative to that in a comparison gas which is 2% $O_2$/98% $N_2$. All of the signals were generated with 10 V across the materials, unless otherwise specified. Blank spaces indicate that there was no detectable signal when that gas composition was contacted with that material. Unless otherwise specified, the gases were measured at 2000 ppm in $N_2$.

TABLE 5b

| | Change in temperature in ° C. | | |
|---|---|---|---|
| | $AlVO_4$ | $BaCuO_{2.5}$ | $Zn_4TiO_6$ |
| CO in $N_2$ | 18.1 | −6 | 6 |
| $N_2$ | 18.1 | −6 | 6 |

Example 6

This example illustrates the use of the AC impedance technique for the measurement of the response of 19 metal oxide semiconducting materials in the presence of 4 gas compositions at 400° C. The signals listed in Table 6 below are the ratios of the magnitudes of the impedances of the materials when exposed to the gas compositions shown to the magnitudes of the impedances in 10,000 ppm $O_2$ in $N_2$. The gases used were 200 ppm $NO_2$ in $N_2$, 200 ppm $NO_2$ and 10,000 ppm $O_2$ in $N_2$, 1000 ppm CO in $N_2$, and $N_2$.

TABLE 6

| | $MgAl_2O_4$ | 1% Zn:$MgAl_2O_4$ | ZnO | $WO_3$ | $NiFe_2O_4$ | $SnO_2$ | $TiO_2$ | $MnTiO_3$ | NiO | $SrNb_2O_6$ |
|---|---|---|---|---|---|---|---|---|---|---|
| $NO_2$ in $N_2$ | 0.6245 | 0.5544 | 55.85 | 8.772 | 5.008 | 9.243 | 1.536 | 0.8643 | 0.5692 | 1.217 |
| $NO_2$ in $O_2$/$N_2$ | 0.7680 | 0.6787 | 47.38 | 9.468 | 12.93 | 10.56 | 1.585 | 0.8475 | 0.9662 | 1.228 |
| CO in $N_2$ | 1.531 | 1.459 | 0.1235 | 0.1865 | 1.248 | 0.0051 | 0.0116 | 37.35 | 9.679 | 0.6501 |
| $N_2$ | 0.8242 | 0.9219 | 4.1290 | 1.716 | 1.327 | 0.3208 | 1.055 | 1.264 | 1.257 | 1.011 |

TABLE 6-continued

|  | CeVO$_4$ | 1% Nb:TiO$_2$ | FeTiO$_3$ | Pr$_6$O$_{11}$ | SrTiO$_3$ | Ba$_2$Cu$_2$O$_5$ | CuMnFe$_2$O$_4$ | LaFeO$_3$ | Zn$_2$V$_2$O$_7$ |
|---|---|---|---|---|---|---|---|---|---|
| NO$_2$ in N$_2$ | 0.9847 | 1.937 | 1.299 | 0.5475 | 0.6524 | 0.7869 | 0.9559 | 0.8401 | 1.209 |
| NO$_2$ in O$_2$/N$_2$ | 1.9977 | 1.674 | 1.034 | 0.5452 | 0.7596 | 0.7834 | 0.9399 | 0.8506 | 1.114 |
| CO in N$_2$ | 1.045 | 0.0112 | 0.6009 | 1.184 | 0.0178 | 0.7603 | 0.6089 | 2037 | 0.8529 |
| N$_2$ | 1.001 | 0.8811 | 1.028 | 1.103 | 1.061 | 1.063 | 1.136 | 1.756 | 0.9900 |

Example 7

This example illustrates the use of the AC impedance technique for the measurement of the response of 19 metal oxide semiconducting materials in the presence of 4 gas compositions at 550° C. The signals listed in the table are from the AC impedance technique. The signals are the ratios of the magnitudes of the impedances of the materials when exposed to the gas compositions shown to the magnitudes of the impedances in 10,000 ppm O$_2$ in N$_2$. The gases used were 200 ppm NO$_2$ in N$_2$, 200 ppm NO$_2$ & 10,000 ppm O$_2$ in N$_2$, 1000 ppm CO in N$_2$, and N$_2$.

TABLE 7

|  | MgAl$_2$O$_4$ | 1% Zn:MgAl$_2$O$_4$ | ZnO | WO$_3$ | NiFe$_2$O$_4$ | SnO$_2$ | TiO$_2$ | MnTiO$_3$ | NiO | SrNb$_2$O$_6$ |
|---|---|---|---|---|---|---|---|---|---|---|
| NO$_2$ in N$_2$ | 0.9894 | 0.9583 | 3.866 | 2.335 | 3.025 | 1.655 | 1.135 | 1.010 | 0.9483 | 1.006 |
| NO$_2$ in O$_2$/N$_2$ | 0.8937 | 0.8984 | 5.272 | 2.006 | 3.553 | 3.390 | 1.314 | 1.014 | 0.5207 | 1.044 |
| CO in N$_2$ | 1.046 | 0.9697 | 0.0133 | 0.2034 | 0.2506 | 0.0069 | 0.0017 | 44.00 | 1.194 | 0.2814 |
| N$_2$ | 1.067 | 1.060 | 0.7285 | 0.9526 | 1.208 | 0.2666 | 0.7263 | 1.280 | 1.341 | 0.9830 |

|  | CeVO$_4$ | 1% Nb:TiO$_2$ | FeTiO$_3$ | Pr$_6$O$_{11}$ | SrTiO$_3$ | Ba$_2$Cu$_2$O$_5$ | CuMnFe$_2$O$_4$ | LaFeO$_3$ | Zn$_2$V$_2$O$_7$ |
|---|---|---|---|---|---|---|---|---|---|
| NO$_2$ in N$_2$ | 1.003 | 1.271 | 1.193 | 1.223 | 0.9055 | 0.7071 | 1.148 | 1.302 | 1.199 |
| NO$_2$ in O$_2$/N$_2$ | 0.9975 | 1.302 | 1.073 | 0.9656 | 0.9881 | 0.3812 | 0.9891 | 0.9429 | 1.086 |
| CO in N$_2$ | 1.104 | 0.0021 | 0.6743 | 62.76 | 0.0029 | 3.0892 | 2.557 | 123.3 | 0.4726 |
| N$_2$ | 1.024 | 0.477 | 1.054 | 1.495 | 1.210 | 1.333 | 1.681 | 1.789 | 0.9034 |

Example 8

This example illustrates the use of the AC impedance technique for the measurement of the response of 23 semiconducting materials in the presence of 4 gas compositions at 650–700° C. The signals listed in the table are from the AC impedance technique. The signals are the ratios of the magnitudes of the impedances of the materials when exposed to the gas compositions shown to the magnitudes of the impedances in 10,000 ppm O$_2$ in N$_2$. The gases used were 200 ppm NO$_2$ in N$_2$, 200 ppm NO$_2$ & 10,000 ppm O$_2$ in N$_2$, 1000 ppm CO in N$_2$, and N$_2$.

TABLE 8

|  | MgAl$_2$O$_4$ | 1% Zn:MgAl$_2$O$_4$ | ZnO | WO$_3$ | NiFe$_2$O$_4$ | SnO$_2$ | TiO$_2$ | MnTiO$_3$ | NiO | SrNb$_2$O$_6$ | CeVO$_4$ | 1% Nb:TiO$_2$ |
|---|---|---|---|---|---|---|---|---|---|---|---|---|
| NO$_2$ in N$_2$ | 0.9450 | 1.022 | 0.4876 | 0.7151 | 0.5807 | 0.5419 | 0.5617 | 1.445 | 1.379 | 0.8852 | 1.050 | 0.5711 |
| NO$_2$ in O$_2$/N$_2$ | 0.6412 | 0.8310 | 1.235 | 1.281 | 1.105 | 0.8265 | 1.030 | 0.9561 | 0.8127 | 0.9862 | 1.135 | 0.8263 |
| CO in N$_2$ | 0.9074 | 0.9684 | 0.0348 | 0.2693 | 0.0408 | 0.0238 | 0.0015 | 113.3 | 1.782 | 0.0301 | 1.565 | 0.0035 |
| N$_2$ | 1.056 | 1.100 | 0.2753 | 0.6332 | 0.4421 | 0.3521 | 0.3957 | 1.877 | 1.409 | 0.8788 | 1.080 | 0.2802 |

|  | FeTiO$_3$ | Pr$_6$O$_{11}$ | SrTiO$_3$ | Ba$_2$Cu$_2$O$_5$ | CuMnFe$_2$O$_4$ | LaFeO$_3$ | Zn$_2$V$_2$O$_7$ | ZnO + 2.5% F2889 | ZnO + 10% F3876 | SnO$_2$ + 5% F2889 | WO$_3$ + 10% F3876 |
|---|---|---|---|---|---|---|---|---|---|---|---|
| NO$_2$ in N$_2$ | 0.9072 | 1.516 | 1.051 | 0.5615 | 3.401 | 1.331 | 0.8631 | 0.5810 | 0.7944 | 0.6270 | 0.6055 |
| NO$_2$ in O$_2$/N$_2$ | 0.9524 | 0.9814 | 0.9320 | 0.9703 | 1.001 | 1.013 | 0.9459 | 1.141 | 1.176 | 0.8927 | 1.284 |
| CO in N$_2$ | 0.4346 | 8005 | 0.0020 | 381.3 | 2.198 | 43.11 | 0.4672 | 0.0020 | 0.0016 | 0.0043 | 0.0122 |
| N$_2$ | 0.8050 | 1.962 | 1.076 | 1.308 | 4.250 | 1.673 | 0.6574 | 0.1054 | 0.1338 | 0.2780 | 0.4862 |

Example 9

This example illustrates the use of the AC impedance technique for the measurement of the response of 16 semiconducting materials in the presence of 4 gas compositions at 800° C. The signals listed in the table are from the AC impedance technique. The signals are the ratios of the magnitudes of the impedances of the materials when exposed to the gas compositions shown to the magnitudes of the impedances in 10,000 ppm $O_2$ in $N_2$. The gases used were 200 ppm $NO_2$ in $N_2$, 200 ppm $NO_2$ & 10,000 ppm $O_2$ in $N_2$, 1000 ppm CO in $N_2$, and $N_2$.

TABLE 9

|  | ZnO | $WO_3$ | $NiFe_2O_4$ | $SnO_2$ | $TiO_2$ | $MnTiO_3$ | NiO | $SrNb_2O_6$ | $CeVO_4$ |
|---|---|---|---|---|---|---|---|---|---|
| $NO_2$ in $N_2$ | 0.3980 | 0.5737 | 0.6710 | 0.4050 | 0.4859 | 1.981 | 1.917 | 0.7555 | 1.013 |
| $NO_2$ in $O_2$/$N_2$ | 1.594 | 1.117 | 4.795 | 6.456 | 1.052 | 1.497 | 0.8529 | 0.9928 | 1.058 |
| CO in $N_2$ | 0.688 | 0.2610 | 0.0642 | 0.2349 | 0.0014 | 123.2 | 5.129 | 0.0144 | 2.165 |
| $N_2$ | 0.3070 | 0.5103 | 0.5339 | 0.2852 | 0.3093 | 2.882 | 2.124 | 0.5167 | 1.075 |

|  | 1% $Nb:TiO_2$ | $FeTiO_3$ | $Pr_6O_{11}$ | $SrTiO_3$ | $Ba_2Cu_2O_5$ | $CuMnFe_2O_4$ | $LaFeO_3$ |
|---|---|---|---|---|---|---|---|
| $NO_2$ in $N_2$ | 0.3280 | 0.6799 | 1.569 | 0.0049 | 4.061 | 2.869 | 1.252 |
| $NO_2$ in $O_2$/$N_2$ | 1.006 | 0.9982 | 1.010 | 0.0260 | 0.9811 | 0.9389 | 1.326 |
| CO in $N_2$ | 0.0047 | 0.2831 | 3530 | 1.004 | 216.0 | 0.8810 | 63.36 |
| $N_2$ | 0.1960 | 0.5600 | 2.999 | 1.048 | 7.445 | 3.413 | 1.612 |

What is claimed is:

1. An apparatus for analyzing a multi-component gas mixture, comprising:
   (a) an array of at least two chemo/electro-active materials, each chemo/electro-active material exhibiting a different electrical response characteristic, upon exposure at a selected temperature to the gas mixture, than each of the other chemo/electro-active materials, the electrical response characteristic of at least one material being quantifiable as value, wherein the value of the response of that material is constant or varies by no more than about twenty percent during exposure of the material to the gas mixture at the selected temperature for a period of at least about one minute;
   (b) a heater that heats the array to a temperature above 500° C.;
   (c) means for determining the electrical response of each chemo/electro-active material upon exposure of the array to the gas mixture; and
   (d) means for detecting the presence of, or calculating the actual concentration of, one or more individual component gases and/or subgroups within the gas mixture from the electrical responses of the chemo/electro-active materials inputted thereto, but not from a baseline response value, comparison response value or reference gas value inputted thereto.

2. An apparatus according to claim 1 wherein the array is situated within the gas mixture, and the gas mixture has a temperature of about 400° C. or more.

3. An apparatus according to claim 1 wherein the gas mixture is an emission from a combustion process.

4. An apparatus according to claim 1 further comprising means for calculating the concentration within the gas mixture of at least one individual gas component.

5. An apparatus according to claim 1 wherein the electrical response is selected from the group consisting of resistance, impedance, capacitance, voltage or current.

6. An apparatus according to claim 1 wherein at least one chemo/electro-active material is a metal oxide.

7. An apparatus according to claim 1 wherein the multi-component gas mixture is emitted by a process, or is a product of a chemical reaction that is transmitted to a device, and wherein the apparatus further comprises means for utilizing the electrical responses for controlling the process or the device.

8. An apparatus according to claim 1 wherein the component gases in the gas mixture are not separated.

9. An apparatus according to claim 1 comprising means for calculating the concentration within the gas mixture of at least one individual gas component.

10. An apparatus according to claim 1 wherein at least one chemo/electro-active material, when at a temperature of about 400° C. or more, (a) has an electrical resistivity in the range of about 1 ohm-cm to about $10^6$ ohm-cm, and (b) exhibits a change in electrical resistance of at least about 0.1 percent upon exposure of the material to the gas mixture, as compared to the resistance before exposure.

11. An apparatus according to claim 1 wherein the gas mixture has a temperature of less than 400° C.

12. An apparatus according to claim 6 wherein the chemo/electro-active materials comprise:
   an array of first and second chemo/electro-active materials, each chemo/electro-active material exhibiting a different electrical response characteristic, upon exposure at a selected temperature to the gas mixture, than each of the other chemo/electro-active materials, wherein the chemo/electro-active materials are selected from the pairings in the group consisting of
   (a) the first material is $M^1O_x$, and the second material is $M^1_aM^2_bO_x$;
   (b) the first material is $M^1O_x$, and the second material is $M^1_aM^2_bM^3_cO_x$;
   (c) the first material is $M^1_aM^2_bO_x$, and the second material is $M^1_aM^2_bM^3_cO_x$;
   (d) the first material is a first $M^1O_x$, and the second material is a second $M^1O_x$;
   (e) the first material is a first $M^1_aM^2_bO_x$, and the second material is a second $M^1_aM^2_bO_x$; and
   (f) the first material is a first $M^1_aM^2_bM^3_cO_x$, and the second material is a second $M^1_aM^2_bM^3_cO_x$;
   wherein $M^1$ is selected from the group consisting of Ce, Co, Cu, Fe, Ga, Nb, Ni, Pr, Ru, Sn, Ti, Tm, W, Yb, Zn, and Zr; $M^2$ and $M^3$ are each independently selected from the group consisting of Al, Ba, Bi, Ca, Cd, Ce, Co, Cr, Cu, Fe, Ga, Ge, In, K, La, Mg, Mn, Mo, Na, Nb, Ni, Pb, Pr, Rb, Ru, Sb, Sc, Si, Sn, Sr, Ta, Ti, Tm, V, W, Y, Yb, Zn, and Zr, but $M^2$ and $M^3$ are not the same in $M^1{}_aM^2{}_bM^3{}_cO_x$;

a, b and c are each independently about 0.0005 to about 1; and x is a number sufficient so that the oxygen present balances the charges of the other elements in the compound.

13. An apparatus according to claim 6 wherein the chemo/electro-active materials comprise an array of chemo/electro-active materials, each chemo/electro-active material exhibiting a different electrical response characteristic, upon exposure at a selected temperature to the gas mixture, than each of the other chemo/electro-active materials, wherein at least one chemo/electro-active material is selected from the group consisting of $M^1O_x$, $M^1{}_aM^2{}_bO_x$ and $M^1{}_aM^2{}_bM^3{}_cO_x$;

wherein $M^1$ is selected from the group consisting of Ce, Co, Cu, Fe, Ga, Nb, Ni, Pr, Ru, Sn, Ti, Tm, W, Yb, Zn, and Zr;

$M^2$ and $M^3$ are each independently selected from the group consisting of Al, Ba, Bi, Ca, Cd, Ce, Co, Cr, Cu, Fe, Ga, Ge, In, K, La, Mg, Mn, Mo, Na, Nb, Ni, Pb, Pr, Rb, Ru, Sb, Sc, Si, Sn, Sr, Ta, Ti, Tm, V, W, Y, Yb, Zn, and Zr, but $M^2$ and $M^3$ are not the same in $M^1{}_aM^2{}_bM^3{}_cO_x$;

a, b and c are each independently about 0.0005 to about 1; and x is a number sufficient so that the oxygen present balances the charges of the other elements in the compound.

14. An apparatus according to claim 1 wherein the gas mixture comprises one or more members of the group consisting of oxygen, carbon monoxide, a nitrogen oxide, a hydrocarbon, $CO_2$, $H_2S$, sulfur dioxide, a halogen, hydrogen, water vapor, ammonia, alcohol, a solvent vapor, an ether, a ketone, an aldehyde, a carbonyl, and a microorganism.

15. An apparatus according to claim 1 wherein the gas mixture comprises one or more members of the group consisting of oxygen, a nitrogen oxide, a hydrocarbon, and ammonia.

16. An apparatus according to claim 1 wherein the gas mixture comprises one or more members of the group consisting of a nitrogen oxide and ammonia.

17. An apparatus according to claim 1 wherein the gas mixture comprises one or more members of the group consisting of oxygen and a hydrocarbon.

18. An apparatus according to claim 1 wherein the gas mixture is provided from a manufacturing process, a waste stream, environmental monitoring, or a medical, agriculture, food or beverage operation.

19. An apparatus for analyzing a multi-component gas mixture, comprising:

(a) an array of first and second chemo/electro-active materials, each chemo/electro-active material exhibiting a different electrical response characteristic, upon exposure at a selected temperature to the gas mixture, than each of the other chemo-electro-active materials, wherein the chemo/electro-active materials are selected from the pairings in the group consisting of (i) the first material is $M^1O_x$, and the second material is $M^1{}_aM^2{}_bO_x$;

(ii) the first material is $M^1O_x$, and the second material is $M^1{}_aM^2{}_bM^3{}_cO_x$;

(iii) the first material is $M^1{}_aM^2{}_bO_x$, and the second material is $M^1{}_aM^2{}_bM^3{}_cO_x$;

(iv) the first material is a first $M^1O_x$, and the second material is a second $M^1O_x$;

(v) the first material is a first $M^1{}_aM^2{}_bO_x$, and the second material is a second $M^1{}_aM^2{}_bO_x$; and (vi) the first material is a first $M^1{}_aM^2{}_bM^3{}_cO_x$, and the second material is a second $M^1{}_aM^2{}_bM^3{}_cO_x$;

wherein $M^1$ is selected from the group consisting of Ce, Co, Cu, Fe, Ga, Nb, Ni, Pr, Ru, Sn, Ti, Tm, W, Yb, Zn, and Zr; $M^2$ and $M^3$ are each independently selected from the group consisting of Al, Ba, Bi, Ca, Cd, Ce, Co, Cr, Cu, Fe, Ga, Ge, In, K, La, Mg, Mn, Mo, Na, Nb, Ni, Pb, Pr, Rb, Ru, Sb, Sc, Si, Sn, Sr, Ta, Ti, Tm, V, W, Y, Yb, Zn, and Zr, but $M^2$ and $M^3$ are not the same in $M^1{}_aM^2{}_bM^3{}_cO_x$; a, b and c are each independently about 0.0005 to about 1; and is a number sufficient so that the oxygen present balances the charges of the other elements in the compound;

(b) a heater that heats the array to a temperature above 500° C.;

(c) means for determining the electrical response of each chemo/electro-active material upon exposure of the array to the gas mixture; and (d) means for detecting the presence of, or calculating the actual concentration of, one or more individual component gases and/or subgroups within the gas mixture from the electrical responses of the chemo/electro-active materials inputted thereto, but not from a baseline response value, comparison response value or reference gas value inputted thereto.

20. An apparatus according to claim 19 wherein (a) $M^1O_x$ is selected from the group consisting of $Ce_aO_x$, $CoO_x$, $CuO_x$, $FeO_x$, $GaO_x$, $NbO_x$, $NiO_x$, $PrO_x$, $RuO_x$, $SnO_x$, $Ta_aO_x$, $TiO_x$, $TmO_x$, $WO_x$, $YbO_x$, $ZnO_x$, $ZrO_x$, $SnO_x$ with Ag additive, $ZnO_x$ with Ag additive, $TiO_x$ with Pt additive, $ZnO_x$ with frit additive, $NiO_x$ with frit additive, $SnO_x$ with frit additive, or $WO_x$ with frit additive;

(b) $M^1{}_aM^2{}_bO_x$ is selected from the group consisting of $Al_aCr_bO_x$, $Al_aFe_bO_x$, $Al_aMg_bO_x$, $Al_aNi_bO_x$, $Al_aTi_bO_x$, $Al_aV_bO_x$, $Ba_aCu_bO_x$, $Ba_aSn_bO_x$, $Ba_aZn_bO_x$, $Bi_aRu_bO_x$, $Bi_aSn_bO_x$, $Bi_aZn_bO_x$, $Ca_aSn_bO_x$, $Ca_aZn_bO_x$, $Cd_aSn_bO_x$, $Cd_aZn_bO_x$, $Ce_aFe_bO_x$, $Ce_aNb_bO_x$, $Ce_aTi_bO_x$, $Ce_aV_bO_x$, $Co_aCu_bO_x$, $Co_aGe_bO_x$, $Co_aLa_bO_x$, $Co_aMg_bO_x$, $Co_aNb_bO_x$, $Co_aPb_bO_x$, $Co_aSn_bO_x$, $Co_aV_bO_x$, $Co_aW_bO_x$, $Co_aZn_bO_x$, $Cr_aCu_bO_x$, $Cr_aLa_bO_x$, $Cr_aMn_bO_x$, $Cr_aNi_bO_x$, $Cr_aSi_bO_x$, $Cr_aTi_bO_x$, $Cr_aY_bO_x$, $Cr_aZn_bO_x$, $Cu_aFe_bO_x$, $Cu_aGa_bO_x$, $Cu_aLa_bO_x$, $Cu_aNa_bO_x$, $Cu_aNi_bO_x$, $Cu_aPb_bO_x$, $Cu_aSn_bO_x$, $Cu_aSr_bO_x$, $Cu_aTi_bO_x$, $Cu_aZn_bO_x$, $Cu_aZr_bO_x$, $Fe_aGa_bO_x$, $Fe_aLa_bO_x$, $Fe_aMo_bO_x$, $Fe_aNb_bO_x$, $Fe_aNi_bO_x$, $Fe_aSn_bO_x$, $Fe_aTi_bO_x$, $Fe_aW_bO_x$, $Fe_aZn_bO_x$, $Fe_aZr_bO_x$, $Ga_aLa_bO_x$, $Ga_aSn_bO_x$, $Ge_aNb_bO_x$, $Ge_aTi_bO_x$, $In_aSn_bO_x$, $K_aNb_bO_x$, $Mn_aNb_bO_x$, $Mn_aSn_bO_x$, $Mn_aTi_bO_x$, $Mn_aY_bO_x$, $Mn_aZn_bO_x$, $Mo_aPb_bO_x$, $Mo_aRb_bO_x$, $Mo_aSn_bO_x$, $Mo_aTi_bO_x$, $Mo_aZn_bO_x$, $Nb_aNi_bO_x$, $Nb_aNi_bO_x$, $Nb_aSr_bO_x$, $Nb_aTi_bO_x$, $Nb_aW_bO_x$, $Nb_aZr_bO_x$, $Ni_aSi_bO_x$, $Ni_aSn_bO_x$, $Ni_aY_bO_x$, $Ni_aZn_bO_x$, $Ni_aZr_bO_x$, $Pb_aSn_bO_x$, $Pb_aZn_bO_x$, $Rb_aW_bO_x$, $Ru_aSn_bO_x$, $Ru_aW_bO_x$, $Ru_aZn_bO_x$, $Sb_aSn_bO_x$, $Sb_aZn_bO_x$, $Sc_aZr_bO_x$, $Si_aSn_bO_x$, $Si_aTi_bO_x$, $Si_aW_bO_x$, $Si_aZn_bO_x$, $Sn_aTa_bO_x$, $Sn_aTi_bO_x$, $Sn_aW_bO_x$, $Sn_aZn_bO_x$, $Sn_aZr_bO_x$, $Sr_aTi_bO_x$, $Ta_aTi_bO_x$, $Ta_aZn_bO_x$, $Ta_aZr_bO_x$, $Ti_aV_bO_x$, $Ti_aW_bO_x$, $Ti_aZn_bO_x$, $Ti_aZr_bO_x$, $V_aZn_bO_x$, $V_aZr_bO_x$, $W_aZn_bO_x$, $W_aZr_bO_x$, $Y_aZr_bO_x$, $Zn_aZr_bO_x$, $Al_aNi_bO_x$ with frit additive, $Cr_aTi_bO_x$ with frit additive, $Fe_aLa_bO_x$ with frit additive, $Fe_aNi_bO_x$ with frit additive, $Fe_aTi_bO_x$ with frit additive, $Nb_aTi_bO_x$ with frit additive, $Nb_aW_bO_x$ with frit additive, $Ni_aZn_bO_x$ with frit additive, $Ni_aZr_bO_x$ with frit additive, $Sb_aSn_bO_x$ with frit additive, $Ta_aTi_bO_x$ with frit additive, or $Ti_aZn_bO_x$ with frit additive; and/or (c) $M^1{}_aM^2{}_bM^3{}_cO_x$ is selected from the group consisting of $Al_aMg_bZn_cO_x$, $Al_aSi_bV_cO_x$, $Ba_aCu_bTi_cO_x$, $Ca_aCe_bZr_cO_x$, $Co_aNi_bTi_cO_x$, $Co_aNi_bZr_cO_x$, $Co_aPb_bSn_cO_x$, $Co_aPb_bZn_cO_x$, $Cr_aSr_bTi_cO_x$, $Cu_aFe_bMn_cO_x$, $Cu_aLa_bSr_cO_x$, $Fe_aNb_bTi_cO_x$, $Fe_aPb_bZn_cO_x$, $Fe_aSr_bTi_cO_x$, $Fe_aTa_bTi_cO_x$, $Fe_aW_bZr_cO_x$, $Ga_aTi_bZn_cO_x$, $La_aMn_bNa_cO_x$, $La_aMn_bSr_cO_x$, $Mn_aSr_bTi_cO_x$, $Mo_aPb_bZn_cO_x$, $Nb_aSr_bTi_cO_x$, $Nb_aSr_bW_cO_x$, $Nb_aTi_bZn_cO_x$, $Ni_aSr_bTi_cO_x$, $Sn_aW_bZn_cO_x$, $Sr_aTi_bV_cO_x$, $Sr_aTi_bZn_cO_x$, or $Ti_aW_bZr_cO_x$.

21. An apparatus according to claim 19 wherein the array is situated within the gas mixture, and the gas mixture has a temperature of about 400° C. or more.

22. An apparatus according to claim 19 wherein the gas mixture is an emission from a combustion process.

23. An apparatus according to claim 19 wherein the component gases in the gas mixture are not separated.

24. An apparatus according to claim 19 wherein the electrical responses of the chemo/electro-active materials are determined upon exposure to only the multi-component gas mixture.

25. An apparatus according to claim 19 comprising means for calculating the concentration within the gas mixture of at least one individual gas component.

26. An apparatus according to claim 19 further comprising means for measuring the temperature of the gas mixture, and means for digitizing the electrical responses and the temperature measurement.

27. An apparatus according to claim 19 wherein at least one chemo/electro-active material, when at a temperature of about 400° C. or more, (a) has an electrical resistivity in the range of about 1 ohm-cm to about $10^6$ ohm-cm, and (b) exhibits a change in electrical resistance of at least about 0.1 percent upon exposure of the material to the gas mixture, as compared to the resistance before exposure.

28. An apparatus according to claim 19 wherein the electrical response characteristic of at least one material upon exposure to the gas mixture at a selected temperature is quantifiable as a value, and the value of the response of that material is constant or varies by no more than about twenty percent during exposure of the material to the gas mixture at the selected temperature for a period of at least about one minute.

29. An apparatus according to claim 19 wherein the electrical response is selected from the group consisting of resistance, impedance, capacitance, voltage or current.

30. An apparatus according to claim 19 wherein the multi-component gas mixture is emitted by a process, or is a product of a chemical reaction that is transmitted to a device, and wherein the apparatus further comprises means for utilizing the electrical responses for controlling the process or the device.

31. An apparatus according to claim 19 wherein the gas mixture has a temperature of less than 400° C.

32. An apparatus according to claim 19 wherein the gas mixture comprises one or more members of the group consisting of oxygen, carbon monoxide, a nitrogen oxide, a hydrocarbon, $CO_2$, $H_2S$, sulfur dioxide, a halogen, hydrogen, water vapor, ammonia, alcohol, a solvent vapor, an ether, a ketone, an aldehyde, a carbonyl, and a microorganism.

33. An apparatus according to claim 19 wherein the gas mixture comprises one or more members of the group consisting of oxygen, a nitrogen oxide, a hydrocarbon, and ammonia.

34. An apparatus according to claim 19 wherein the gas mixture comprises one or more members of the group consisting of a nitrogen oxide and ammonia.

35. An apparatus according to claim 19 wherein the gas mixture comprises one or more members of the group consisting of oxygen and a hydrocarbon.

36. An apparatus according to claim 19 wherein the gas mixture is provided from a manufacturing process, a waste stream, environmental monitoring, or a medical, agriculture, food or beverage operation.

37. An apparatus for analyzing a multi-component gas mixture, comprising:

(a) an array of chemo/electro-active materials, each chemo/electro-active material exhibiting a different electrical response characteristic, upon exposure at a selected temperature to the gas mixture, than each of the other chemo-electro-active materials, wherein at least one chemo/electro-active materials is selected from the group consisting of $M^1O_x$, $M^1{}_aM^2{}_bO_x$ and $M^1{}_aM^2{}_bM^3{}_cO_x$; wherein $M^1$ is selected from the group consisting of Ce, Co, Cu, e, Ga, Nb, Ni, Pr, Ru, Sn, Ti, Tm, W, Yb, Zn, and Zr; $M^2$ and $M^3$ are each independently selected from the group consisting of Al, Ba, Bi, Ca, Cd, Ce, Co, Cr, Cu, Fe, Ga, Ge, In, K, La, Mg, Mn, Mo, Na, Nb, Ni, Pb, Pr, Rb, Ru, Sb, Sc, Si, Sn, Sr, Ta, Ti, Tm, V, W, Y, Yb, Zn, and Zr, but $M^2$ and $M^3$ are not the same in $M^1{}_aM^2{}_bM^3{}_cO_x$; a, b and c are each independently about 0.0 05 to about 1; and x is a number sufficient so that the oxygen present balances the charges of the other elements in the compound;

(b) a heater that heats the array to a temperature above 500° C.;

(c) means for determining the electrical response of each chemo/electro-active material upon exposure of the array to the gas mixture; and (d) means for detecting the presence of, or calculating the actual concentration of, one or more individual component gases and/or subgroups within the gas mixture from the electrical responses of the chemo/electro-active materials, but not a baseline response value, a comparison response value or a reference gas value.

38. An apparatus according to claim 37 wherein (a) $M^1O_x$ is selected from the group consisting of $Ce_aO_x$, $CoO_x$, $CuO_x$, $FeO_x$, $GaO_x$, $NbO_x$, $NiO_x$, $PrO_x$, $RuO_x$, $SnO_x$, $Ta_aO_x$, $TiO_x$, $TmO_x$, $WO_x$, $YbO_x$, $ZnO_x$, $ZrO_x$, $SnO_x$ with Ag additive, $ZnO_x$ with Ag additive, $TiO_x$ with Pt additive, $ZnO_x$ with frit additive, $NiO_x$ with frit additive, $SnO_x$ with frit additive, or $WO_x$ with frit additive;

(b) $M^1{}_aM^2{}_bO_x$ is selected from the group consisting of $Al_aCr_bO_x$, $Al_aFe_bO_x$, $Al_aMg_bO_x$, $Al_aNi_bO_x$, $Al_aTi_bO_x$, $Al_aV_bO_x$, $Ba_aCu_bO_x$, $Ba_aSn_bO_x$, $Ba_aZn_bO_x$, $Bi_aRu_bO_x$, $Bi_aSn_bO_x$, $Bi_aZn_bO_x$, $Ca_aSn_bO_x$, $Ca_aZn_bO_x$, $Cd_aSn_bO_x$, $Cd_aZn_bO_x$, $Ce_aFe_bO_x$, $Ce_aNb_bO_x$, $Ce_aTi_bO_x$, $Ce_aV_bO_x$, $Co_aCu_bO_x$, $Co_aGe_bO_x$, $Co_aLa_bO_x$, $Co_aMg_bO_x$, $Co_aNb_bO_x$, $Co_aPb_bO_x$, $Co_aSn_bO_x$, $Co_aV_bO_x$, $Co_aW_bO_x$, $Co_aZn_bO_x$, $Cr_aCu_bO_x$, $Cr_aLa_bO_x$, $Cr_aMn_bO_x$, $Cr_aNi_bO_x$, $Cr_aSi_bO_x$, $Cr_aTi_bO_x$, $Cr_aY_bO_x$, $Cr_aZn_bO_x$, $Cu_aFe_bO_x$, $Cu_aGa_bO_x$, $Cu_aLa_bO_x$, $Cu_aNa_bO_x$, $Cu_aNi_bO_x$, $Cu_aPb_bO_x$, $Cu_aSn_bO_x$, $Cu_aSr_bO_x$, $Cu_aTi_bO_x$, $Cu_aZn_bO_x$, $Cu_aZr_bO_x$, $Fe_aGa_bO_x$, $Fe_aLa_bO_x$, $Fe_aMo_bO_x$, $Fe_aNb_bO_x$, $Fe_aNi_bO_x$, $Fe_aSn_bO_x$, $Fe_aTi_bO_x$, $Fe_aW_bO_x$, $Fe_aZn_bO_x$, $Fe_aZr_bO_x$, $Ga_aLa_bO_x$, $Ga_aSn_bO_x$, $Ge_aNb_bO_x$, $Ge_aTi_bO_x$, $In_aSn_bO_x$, $K_aNb_bO_x$, $Mn_aNb_bO_x$, $Mn_aSn_bO_x$, $Mn_aTi_bO_x$, $Mn_aY_bO_x$, $Mn_aZn_bO_x$, $Mo_aPb_bO_x$, $Mo_aRb_bO_x$, $Mo_aSn_bO_x$, $Mo_aTi_bO_x$, $Mo_aZn_bO_x$, $Nb_aNi_bO_x$, $Nb_aNi_bO_x$, $Nb_aSr_bO_x$, $Nb_aTi_bO_x$, $Nb_aW_bO_x$, $Nb_aZr_bO_x$, $Ni_aSi_bO_x$, $Ni_aSn_bO_x$, $Ni_aY_bO_x$, $Ni_aZn_bO_x$, $Ni_aZr_bO_x$, $Pb_aSn_bO_x$, $Pb_aZn_bO_x$, $Rb_aW_bO_x$, $Ru_aSn_bO_x$, $Ru_aW_bO_x$, $Ru_aZn_bO_x$, $Sb_aSn_bO_x$, $Sb_aZn_bO_x$, $Sc_aZr_bO_x$, $Si_aSn_bO_x$, $Si_aTi_bO_x$, $Si_aW_bO_x$, $Si_aZn_bO_x$, $Sn_aTa_bO_x$, $Sn_aTi_bO_x$, $Sn_aW_bO_x$, $Sn_aZn_bO_x$, $Sn_aZr_bO_x$, $Sr_aTi_bO_x$, $Ta_aTi_bO_x$, $Ta_aZn_bO_x$, $Ta_aZr_bO_x$, $Ti_aV_bO_x$, $Ti_aW_bO_x$, $Ti_aZn_bO_x$, $Ti_aZr_bO_x$, $V_aZn_bO_x$, $V_aZr_bO_x$, $W_aZn_bO_x$, $W_aZr_bO_x$, $Y_aZr_bO_x$, $Zn_aZr_bO_x$, $Al_aNi_bO_x$ with frit additive, $Cr_aTi_bO_x$ with frit additive, $Fe_aLa_bO_x$ with frit additive, $Fe_aNi_bO_x$ with frit additive, $Fe_aTi_bO_x$ with frit additive, $Nb_aTi_bO_x$ with frit additive, $Nb_aW_bO_x$ with frit additive, $Ni_aZn_bO_x$ with frit additive, $Ni_aZr_bO_x$ with frit additive, $Sb_aSn_bO_x$ with frit additive, $Ta_aTi_bO_x$ with frit additive, or $Ti_aZn_bO_x$ with frit additive; and/or (c) $M^1{}_aM^2{}_bM^3{}_cO_x$ is selected from the group consisting of $Al_aMg_bZn_cO_x$, $Al_aSi_bV_cO_x$, $Ba_aCu_bTi_cO_x$, $Ca_aCe_bZr_cO_x$, $Co_aNi_bTi_cO_x$, $Co_aNi_bZr_cO_x$, $Co_aPb_bSn_cO_x$, $Co_aPb_bZn_cO_x$, $Cr_aSr_bTi_cO_x$, $Cu_aFe_bMn_cO_x$, $Cu_aLa_bSr_cO_x$, $Fe_aNb_bTi_cO_x$, $Fe_aPb_bZn_cO_x$, $Fe_aSr_bTi_cO_x$, $Fe_aTa_bTi_cO_x$, $Fe_aW_bZr_cO_x$, $Ga_aTi_bZn_cO_x$, $La_aMn_bNa_cO_x$, $La_aMn_bSr_cO_x$, $Mn_aSr_bTi_cO_x$, $Mo_aPb_bZn_cO_x$, $Nb_aSr_bTi_cO_x$, $Nb_aSr_bW_cO_x$, $Nb_aTi_bZn_cO_x$, $Ni_aSr_bTi_cO_x$, $Sn_aW_bZn_cO_x$, $Sr_aTi_bV_cO_x$, $Sr_aTi_bZn_cO_x$, or $Ti_aW_bZr_cO_x$.

39. An apparatus according to claim 37 wherein the array is situated within the gas mixture, and the gas mixture has a temperature of about 400° C. or more.

40. An apparatus according to claim 37 wherein the gas mixture is an emission from a combustion process.

41. An apparatus according to claim 37 wherein the component gases in the gas mixture are not separated.

42. An apparatus according to claim 37 wherein the electrical responses of the chemo/electro-active materials are determined upon exposure to only the multi-component gas mixture.

43. An apparatus according to claim 37 comprising means for calculating the concentration within the gas mixture of at least one individual gas component.

44. An apparatus according to claim 37 further comprising means for measuring the temperature of the gas mixture, and means for digitizing the electrical responses and the temperature measurement.

45. An apparatus according to claim 37 wherein at least one chemo/electro-active material, when at a temperature of about 400° C. or more, (a) has an electrical resistivity in the range of about 1 ohm-cm to about $10^6$ ohm-cm, and (b) exhibits a change in electrical resistance of at least about 0.1 percent upon exposure of the material to the gas mixture, as compared to the resistance before exposure.

46. An apparatus according to claim 37 wherein the electrical response characteristic of at least one material upon exposure to the gas mixture at a selected temperature is quantifiable as a value, and the value of the response of that material is constant or varies by no more than about twenty percent during exposure of the material to the gas mixture at the selected temperature for a period of at least about one minute.

47. An apparatus according to claim 37 wherein the electrical response is selected from the group consisting of resistance, impedance, capacitance, voltage or current.

48. An apparatus according to claim 37 wherein the multi-component gas mixture is emitted by a process, or is a product of a chemical reaction that is transmitted to a device, and wherein the apparatus further comprises means for utilizing the electrical responses for controlling the process or the device.

49. An apparatus according to claim 37 wherein the gas mixture has a temperature of less than 400° C.

50. An apparatus according to claim 37 wherein the gas mixture comprises one or more members of the group consisting of oxygen, carbon monoxide, a nitrogen oxide, a hydrocarbon, $CO_2$, $H_2S$, sulfur dioxide, a halogen, hydrogen, water vapor, ammonia, alcohol, a solvent vapor, an ether, a ketone, an aldehyde, a carbonyl, and a microorganism.

51. An apparatus according to claim 37 wherein the gas mixture comprises one or more members of the group consisting of oxygen, a nitrogen oxide, a hydrocarbon, and ammonia.

52. An apparatus according to claim 37 wherein the gas mixture comprises one or more members of the group consisting of a nitrogen oxide and ammonia.

53. An apparatus according to claim 37 wherein the gas mixture comprises one or more members of the group consisting of oxygen and a hydrocarbon.

54. An apparatus according to claim 37 wherein the gas mixture is provided from a manufacturing process, a waste stream, environmental monitoring, or a medical, agriculture, food or beverage operation.

55. A gas-sensitive apparatus, comprising:
    (a) an array of at least three chemo/electro-active materials, each chemo/electro-active material exhibiting a change in electrical resistance upon exposure to a multi-component gas mixture, wherein at least one chemo/electro-active material, when at a temperature of about 400° C. or more, (i) has an electrical resistivity in the range of about 1 ohm-cm to about $10^6$ ohm-cm, and (ii) exhibits a change in electrical resistance of at least about 0.1 percent upon exposure of the material to the gas mixture, as compared to the resistance before exposure;
    (b) a heater that heats the array to a temperature above 500° C.;
    (c) means for determining the electrical response of each chemo/electro-active material upon exposure of the array to the gas mixture; and
    (d) means for detecting the presence of, or calculating the actual concentration of, one or more individual component gases and/or subgroups within the gas mixture from the electrical responses of the chemo/electro-active materials, but not a baseline response value, a comparison response value or a reference gas value.

56. An apparatus according to claim 55 wherein the electrical response characteristic of at least one material upon exposure to the gas mixture at a selected temperature is quantifiable as a value, and the value of the response of that material is constant or varies by no more than about twenty percent during exposure of the material to the gas mixture at the selected temperature for a period of at least about one minute.

57. An apparatus according to claim 55 further comprising means for determining the temperature of the array.

58. An apparatus according to claim 55 wherein at least one chemo/electro-active material is a metal oxide.

59. An apparatus according to claim 55 wherein the array is situated within the gas mixture, and the gas mixture has a temperature of about 400° C. or more.

60. An apparatus according to claim 55 wherein the gas mixture has a temperature of less than 400° C.

61. An apparatus according to claim 55 wherein the component gases in the gas mixture are not separated.

62. An apparatus according to claim 55 comprising means for calculating the concentration within the gas mixture of at least one individual gas component.

63. An apparatus according to claim 55 wherein the electrical response is selected from the group consisting of resistance, impedance, capacitance, voltage or current.

64. An apparatus according to claim 58 wherein the chemo/electro-active materials comprise:
an array of first and second chemo/electro-active materials, each chemo/electro-active material exhibiting a different electrical response characteristic, upon exposure at a selected temperature to the gas mixture, than each of the other chemo/electro-active materials, wherein the chemo/electro-active materials are selected from the pairings in the group consisting of
(a) the first material is $M^1O_x$, and the second material is $M^1_aM^2_bO_x$;
(b) the first material is $M^1O_x$, and the second material is $M^1_aM^2_bM^3_cO_x$;
(c) the first material is $M^1_aM^2_bO_x$, and the second material is $M^1_aM^2_bM^3_cO_x$;
(d) the first material is a first $M^1O_x$, and the second material is a second $M^1O_x$;
(e) the first material is a first $M^1_aM^2_bO_x$, and the second material is a second $M^1_aM^2_bO_x$; and
(f) the first material is a first $M^1_aM^2_bM^3_cO_x$, and the second material is a second $M^1_aM^2_bM^3_cO_x$;
wherein $M^1$ is selected from the group consisting of Ce, Co, Cu, Fe, Ga, Nb, Ni, Pr, Ru, Sn, Ti, Tm, W, Yb, Zn, and Zr;
$M^2$ and $M^3$ are each independently selected from the group consisting of Al, Ba, Bi, Ca, Cd, Ce, Co, Cr, Cu, Fe, Ga, Ge, In, K, La, Mg, Mn, Mo, Na, Nb, Ni, Pb, Pr, Rb, Ru, Sb, Sc, Si, Sn, Sr, Ta, Ti, Tm, V, W, Y, Yb, Zn, and Zr, but $M^2$ and $M^3$ are not the same in $M^1_aM^2_bM^3_cO_x$;
a, b and c are each independently about 0.0005 to about 1; and
x is a number sufficient so that the oxygen present balances the charges of the other elements in the compound.

65. An apparatus according to claim 58 wherein the chemo/electro-active materials comprise an array of chemo/electro-active materials, each chemo/electro-active material exhibiting a different electrical response characteristic, upon exposure at a selected temperature to the gas mixture, than each of the other chemo/electro-active materials,
wherein at least one chemo/electro-active material is selected from the group consisting of $M^1O_x$, $M^1_aM^2_bO_x$ and $M^1_aM^2_bM^3_cO_x$;
wherein $M^1$ is selected from the group consisting of Ce, Co, Cu, Fe, Ga, Nb, Ni, Pr, Ru, Sn, Ti, Tm, W, Yb, Zn, and Zr; $M^2$ and $M^3$ are each independently selected from the group consisting of Al, Ba, Bi, Ca, Cd, Ce, Co, Cr, Cu, Fe, Ga, Ge, In, K, La, Mg, Mn, Mo Na, Nb, Ni, Pb, Pr, Rb, Ru, Sb, Sc, Si, Sn, Sr, Ta, Ti, Tm, V, W, Y, Yb, Zn, and Zr, but $M^2$ and $M^3$ are not the same in $M^1_aM^2_bM^3_cO_x$;
a, b and c are each independently about 0.0005 to about 1; and
x is a number sufficient so that the oxygen present balances the charges of the other elements in the compound.

66. An apparatus according to claim 55 wherein the gas mixture comprises one or more members of the group consisting of oxygen, carbon monoxide, a nitrogen oxide, a hydrocarbon, $CO_2$, $H_2S$, sulfur dioxide, a halogen, hydrogen, water vapor, ammonia, alcohol, a solvent vapor, an ether, a ketone, an aldehyde, a carbonyl, and a microorganism.

67. An apparatus according to claim 55 wherein the gas mixture comprises one or more members of the group consisting of oxygen, a nitrogen oxide, a hydrocarbon, and ammonia.

68. An apparatus according to claim 55 wherein the gas mixture comprises one or more members of the group consisting of a nitrogen oxide and ammonia.

69. An apparatus according to claim 55 wherein the gas mixture comprises one or more members of the group consisting of oxygen and a hydrocarbon.

70. An apparatus according to claim 55 wherein the gas mixture is an emission from a combustion process.

71. An apparatus according to claim 55 wherein the gas mixture is provided from a manufacturing process, a waste stream, environmental monitoring, or a medical, agriculture, food or beverage operation.

72. An apparatus according to claim 55 wherein the multi-component gas mixture is emitted by a process, or is a product of a chemical reaction that is transmitted to a device, and wherein the apparatus further comprises means for utilizing the electrical responses for controlling the process or the device.

73. An apparatus for analyzing a multi-component gas mixture, comprising:
(a) an array of at least two chemo/electro-active materials, each chemo/electro-active material exhibiting a different electrical response characteristic, upon exposure at a selected temperature to the gas mixture, than each of the other chemo/electro-active materials, the electrical response characteristic of at least one material being quantifiable a value, wherein the value of the response of that material is constant or varies by no more than about twenty percent during exposure of the material to the gas mixture at the selected temperature for a period of at least about one minute;
(b) a heater that heats the array to a temperature above 500° C.;
(c) means for determining the electrical response of each chemo/electro-active material upon exposure of the array to the gas mixture; and
(d) means for detecting the presence of, or calculating the actual concentration of, one or more individual component gases and/or subgroups within the gas mixture from only the electrical responses of the chemo/electro-active materials.

74. An apparatus according to claim 73 wherein the electrical response is selected from the group consisting of resistance, impedance, capacitance, voltage or current.

75. An apparatus according to claim 73 wherein the array is situated within the gas mixture, and the gas mixture has a temperature of about 400° C. or more.

76. An apparatus according to claim 73 wherein the gas mixture has a temperature of less than 400° C.

77. An apparatus according to claim 73 wherein at least one chemo/electro-active material, when at a temperature of about 400° C. or more, (a) has an electrical resistivity in the range of about 1 ohm-cm to about $10^6$ ohm-cm, and (b) exhibits a change in electrical resistance of at least about 0.1 percent upon exposure of the material to the gas mixture, as compared to the resistance before exposure.

78. An apparatus according to claim 73 wherein the electrical response characteristic of at least one material upon exposure to the gas mixture at a selected temperature is quantifiable as a value, and the value of the response of that material is constant or varies by no more than about twenty percent during exposure of the material to the gas mixture at the selected temperature for period of at least about one minute.

79. An apparatus according to claim 73 wherein the component gases in the gas mixture are not separated.

80. An apparatus according to claim 73 comprising means for calculating the concentration within the gas mixture of at least one individual gas component.

81. An apparatus according to claim 73 wherein the chemo/electro-active materials comprise an array of first and second chemo/electro-active materials, each chemo/electro active material exhibiting a different electrical response characteristic, upon exposure at a selected temperature to the gas mixture, than each of the other chemo/electro-active materials, wherein the chem/electro-active materials are selected from the pairings in the group consisting of
  (a) the first material is $M^1O_x$, and the second material is $M^1_aM^2_bO_x$;
  (b) the first material is $M^1O_x$, and the second material is $M^1_aM^2_bM^3_cO_x$;
  (c) the first material is $M^1_aM^2_bO_x$, and the second material is $M^1_aM^2_bM^3_cO_x$;
  (d) the first material is a first $M^1O_x$, and the second material is a second $M^1O_x$;
  (e) the first material is a first $M^1_aM^2_bO_x$, and the second material is a second $M^1_aM^2_bO_x$; and
  (f) the first material is a first $M^1_aM^2_bM^3_cO_x$, and the second material is a second $M^1_aM^2_bM^3_cO_x$;
wherein $M^1$ is selected from the group consisting of Ce, Co, Cu, Fe, Ga, Nb, Ni, Pr, Ru, Sn, Ti, Tm, W, Yb, Zn, and Zr;
  $M^2$ and $M^3$ are each independently selected from the group consisting of Al, Ba, Bi, Ca, Cd, Ce, Co, Cr, Cu, Fe, Ga, Ge, In, K, La, Mg, Mn, Mo, Na, Nb, Ni, Pb, Pr, Rb, Ru, Sb, Sc, Si, Sn, Sr, Ta, Ti, Tm, V, W, Y, Yb, Zn, and Zr, but $M^2$ and $M^3$ are not the same in $M^1_aM^2_bM^3_cO_x$;
  a, b and c are each independently about 0.0005 to about 1; and
  x is a number sufficient so that the oxygen present balances the charges of the other elements in the compound.

82. An apparatus according to claim 73 wherein the chemo/electro-active materials comprise an array of chemo/electro-active materials, each chemo/electro active material exhibiting a different electrical response characteristic, upon exposure at a selected temperature to the gas mixture, than each of the other chemo/electro-active materials,
  wherein at least one chem/electro-active materials is selected from the group consisting of $M^1O_x$, $M^1_aM^2_bO_x$ and $M^1_aM^2_bM^3_cO_x$;
  wherein $M^1$ is selected from the group consisting of Ce, Co, Cu, Fe, Ga, Nb, Ni, Pr, Ru, Sn, Ti, Tm, W, Yb, Zn, and Zr; $M^2$ and $M^3$ are each independently selected from the group consisting of Al, Ba, Bi, Ca, Cd, Ce, Co, Cr, Cu, Fe, Ga, Ge, In, K, La, Mg, Mn, Mo, Na, Nb, Ni, Pb, Pr, Rb, Ru, Sb, Sc, Si, Sn, Sr, Ta, Ti, Tm, V, W, Y, Yb, Zn, and Zr, but $M^2$ and $M^3$ are not the same in $M^1_aM^2_bM^3_cO_x$;
  a, b and c are each independently about 0.0005 to about 1; and
  x is a number sufficient so that the oxygen present balances the charges of the other elements in the compound.

83. An apparatus according to claim 73 wherein the gas mixture comprises one or more members of the group consisting of oxygen, carbon monoxide, a nitrogen oxide, a hydrocarbon, $CO_2$, $H_2S$, sulfur dioxide, a halogen, hydrogen, water vapor, ammonia, alcohol, a solvent vapor, an ether, a ketone, an aldehyde, a carbonyl, and a microorganism.

84. An apparatus according to claim 73 wherein the gas mixture comprises one or more members of the group consisting of oxygen, a nitrogen oxide, a hydrocarbon, and ammonia.

85. An apparatus according to claim 73 wherein the gas mixture comprises one or more members of the group consisting of a nitrogen oxide and ammonia.

86. An apparatus according to claim 73 wherein the gas mixture comprises one or more members of the group consisting of oxygen and a hydrocarbon.

87. An apparatus according to claim 73 wherein the gas mixture is an emission from a combustion process.

88. An apparatus according to claim 73 wherein the gas mixture is provided from a manufacturing process, a waste stream, environmental monitoring, or a medical, agriculture, food or beverage operation.

89. An apparatus according to claim 73 wherein the multi-component gas mixture is emitted by a process, or is a product of a chemical reaction that is transmitted to a device, and wherein the apparatus further comprises means for utilizing the electrical responses for controlling the process or the device.

90. An apparatus for analyzing a multi-component gas mixture, comprising:
  (a) an array of first and second chemo/electro-active materials, each chemo/electro-active material exhibiting a different electrical response characteristic, upon exposure at a selected temperature to the gas mixture, than each of the other chemo-electro-active materials, wherein the chemo/electro-active materials are selected from the pairings in the group consisting of
    (i) the first material is $M^1O_x$, and the second material is $M^1_aM^2_bO_x$;
    (ii) the first material is $M^1O_x$, and the second material is $M^1_aM^2_bM^3_cO_x$;
    (iii) the first material is $M^1_aM^2_bO_x$, and the second material is $M^1_aM^2_bM^3_cO_x$;
    (iv) the first material is a first $M^1O_x$, and the second material is a second $M^1O_x$;
    (v) the first material is a first $M^1_aM^2_bO_x$, and the second material is a second $M^1_aM^2_bO_x$; and
    (vi) the first material is a first $M^1_aM^2_bM^3_cO_x$, and the second material is a second $M^1_aM^2_bM^3_cO_x$;
  wherein $M^1$ is selected from the group consisting of Ce, Co, Cu, Fe, Ga, Nb, Ni Pr, Ru, Sn, Ti, Tm, W, Yb, Zn, and Zr; $M^2$ and $M^3$ are each independently selected from the up consisting of Al, Ba, Bi, Ca, Cd, Ce, Co, Cr, Cu, Fe, Ga, Ge, In, K, La, Mg, Mn, Mo, Na, Nb Ni, Pb, Pr, Rb, Ru, Sb, Sc, Si, Sn, Sr, Ta, Ti, Tm, V, W, Y, Yb, Zn, and Zr, but $M^2$ and $M^3$ are not the same in $M^1_aM^2_bM^3_cO_x$; a, b and c are each independently about 0.0005 to about 1; and is a number sufficient so that the oxygen present balances the charges of the other elements in the compound;
  (b) a heater that heats the array to a temperature above 500° C.;
  (c) means for determining the electrical response of each chemo/electro-active material upon exposure of the array to the gas mixture; and
  (d) means for detecting the presence of, or calculating the actual concentration of, one or more individual component gases and/or subgroups within the gas mixture from only the electrical responses of the chemo/electro-active materials.

91. An apparatus according to claim 90 wherein the electrical response is selected from the group consisting of resistance, impedance, capacitance, voltage or current.

92. An apparatus according to claim 90 wherein the array is situated within the gas mixture, and the gas mixture has a temperature of about 400° C. or more.

93. An apparatus according to claim 90 wherein the gas mixture has a temperature of less than 400° C.

94. An apparatus according to claim 90 wherein at least one chemo/electro-active material, when at a temperature of about 400° C. or more, (a) has an electrical resistivity in the range of about 1 ohm-cm to about $10^6$ ohm-cm, and (b) exhibits a change in electrical resistance of at least about 0.1 percent upon exposure of the material to the gas mixture, as compared to the resistance before exposure.

95. An apparatus according to claim 90 wherein the electrical response characteristic of at least one material upon exposure to the gas mixture at a selected temperature is quantifiable as a value, and the value of the response of that material is constant or varies by no more than about twenty percent during exposure of the material to the gas mixture at the selected temperature for a period of at least about one minute.

96. An apparatus according to claim 90 wherein the component gases in the gas mixture are not separated.

97. An apparatus according to claim 90 comprising means for calculating the concentration within the gas mixture of at least one individual gas component.

98. An apparatus according to claim 90 wherein the gas mixture comprises one or more members of the group consisting of oxygen, carbon monoxide, a nitrogen oxide, a hydrocarbon, $CO_2$, $H_2S$, sulfur dioxide, a halogen, hydrogen, water vapor, ammonia, alcohol, a solvent vapor, an ether, a ketone, an aldehyde, a carbonyl, and a microorganism.

99. An apparatus according to claim 90 wherein the gas mixture comprises one or more members of the group consisting of oxygen, a nitrogen oxide, a hydrocarbon, and ammonia.

100. An apparatus according to claim 90 wherein the gas mixture comprises one or more members of the group consisting of a nitrogen oxide and ammonia.

101. An apparatus according to claim 90 wherein the gas mixture comprises one or more members of the group consisting of oxygen and a hydrocarbon.

102. An apparatus according to claim 90 wherein the gas mixture is an emission from a combustion process.

103. An apparatus according to claim 90 wherein the gas mixture is provided from a manufacturing process, a waste stream, environmental monitoring, or a medical, agriculture, food or beverage operation.

104. An apparatus according to claim 90 wherein the multi-component gas mixture is emitted by a process, or is a product of a chemical reaction that is transmitted to a device, and wherein the apparatus further comprises means for utilizing the electrical responses for controlling the process or the device.

105. An apparatus for analyzing a multi-component gas mixture, comprising:
(a) an array of chemo/electro-active materials, each chemo/electro-active material exhibiting a different electrical response characteristic, upon exposure at a selected temperature to the gas mixture, than each of the other chemo-electro-active materials, wherein at least one chemo/electro-active materials is selected from the group consisting of $M^1O_x$, $M^1_aM^2_bO_x$ and $M^1_aM^2_bM^3_cO_x$; wherein $M^1$ is selected from the group consisting of Ce, Co, Cu, Fe, Ga, Nb, Ni, Pr, Ru, Sn, Ti, Tm, W, Yb, Zn, and Zr, $M^2$ and $M^3$ are each independently selected from the group consisting of Al, Ba, Bi, Ca, Cd, Ce, Co, Cr, Cu, Fe, Ga, Ge, In, K, La, Mg, Mn, Mo, Na, Nb, Ni, Pb, Pr, Rb, Ru, Sb, Sc, Si, Sn, Sr, Ta, Ti, Tm, V, W, Y, Yb, Zn, and Zr, but $M^2$ and $M^3$ are not the same in $M^1_aM^2_bM^3_cO_x$; a, b and c are each independently about 0.005 to about 1; and x is a number sufficient so that the oxygen present balances the charges of the other elements in the compound;
(b) a heater that heats the array to a temperature above 500° C.;
(c) means for determining the electrical response of each chemo/electro-active material upon exposure of the array to the gas mixture; and
(d) means for detecting the presence of, or calculating the actual concentration of, one or more individual component gases and/or subgroups within the gas mixture from only the electrical responses of the chemo/electro-active materials.

106. An apparatus according to claim 105 wherein the electrical response is selected from the group consisting of resistance, impedance, capacitance, voltage or current.

107. An apparatus according to claim 105 wherein the array is situated within the gas mixture, and the gas mixture has a temperature of about 400° C. or more.

108. An apparatus according to claim 105 wherein the gas mixture has a temperature of less than 400° C.

109. An apparatus according to claim 105 wherein at least one chemo/electro-active material, when at a temperature of about 400° C. or more, (a) has an electrical resistivity in the range of about 1 ohm-cm to about $10^6$ ohm-cm, and (b) exhibits a change in electrical resistance of at least about 0.1 percent upon exposure of the material to the gas mixture, as compared to the resistance before exposure.

110. An apparatus according to claim 105 wherein the electrical response characteristic of at least one material upon exposure to the gas mixture at a selected temperature is quantifiable as a value, and the value of the response of that material is constant or varies by no more than about twenty percent during exposure of the material to the gas mixture at the selected temperature for a period of at least about one minute.

111. An apparatus according to claim 105 wherein the component gases in the gas mixture are not separated.

112. An apparatus according to claim 105 comprising means for calculating the concentration within the gas mixture of at least one individual gas component.

113. An apparatus according to claim 105 wherein the gas mixture comprises one or more members of the group consisting of oxygen, carbon monoxide, a nitrogen oxide, a hydrocarbon, $CO_2$, $H_2S$, sulfur dioxide, a halogen, hydrogen, water vapor, ammonia, alcohol, a solvent vapor, an ether, a ketone, an aldehyde, a carbonyl, and a microorganism.

114. An apparatus according to claim 105 wherein the gas mixture comprises one or more members of the group consisting of oxygen, a nitrogen oxide, a hydrocarbon, and ammonia.

115. An apparatus according to claim 105 wherein the gas mixture comprises one or more members of the group consisting of a nitrogen oxide and ammonia.

116. An apparatus according to claim 105 wherein the gas mixture comprises one or more members of the group consisting of oxygen and a hydrocarbon.

117. An apparatus according to claim 105 wherein the gas mixture is an emission from a combustion process.

118. An apparatus according to claim 105 wherein the gas mixture is provided from a manufacturing process, a waste stream, environmental monitoring, or a medical, agriculture, food or beverage operation.

119. An apparatus according to claim 105 wherein the multi-component gas mixture is emitted by a process, or is a product of a chemical reaction that is transmitted to a device, and wherein the apparatus further comprises means for utilizing the electrical responses for controlling the process or the device.

120. A gas-sensitive apparatus, comprising:
(a) an array of at least three chemo/electro-active materials, each chemo/electro-active material exhibiting a change in electrical resistance upon exposure to a multi-component gas mixture, wherein at least one chemo/electro-active material, when at a temperature of about 400° C. or more, (i) has an electrical resistivity in the range of about 1 ohm-cm to bout $10^6$ ohm-cm, and (ii) exhibits a change in electrical resistance of at least about 0.1 percent upon exposure of the material to the gas mixture, as compared to the resistance before exposure;
(b) a heater that heats the array to a temperature above 500° C.;
(c) means for determining the electrical response of each chemo/electro-active material upon exposure of the array to the gas mixture; and
(d) means for detecting the presence of, or calculating the actual concentration of, one or more individual component gases and/or subgroups within the gas mixture from only the electrical responses of the chemo/electro-active materials.

121. An apparatus according to claim 120 wherein the electrical response is selected from the group consisting of resistance, impedance, capacitance, voltage or current.

122. An apparatus according to claim 120 wherein the array is situated within the gas mixture, and the gas mixture has a temperature of about 400° C. or more.

123. An apparatus according to claim 120 wherein the gas mixture has a temperature of less than 400° C.

124. An apparatus according to claim 120 wherein at least one chemo/electro-active material, when at a temperature of about 400° C. or more, (a) has an electrical resistivity in the range of about 1 ohm-cm to about $10^6$ ohm-cm, and (b) exhibits a change in electrical resistance of at least about 0.1 percent upon exposure of the material to the gas mixture, as compared to the resistance before exposure.

125. An apparatus according to claim 120 wherein the electrical response characteristic of at least one material upon exposure to the gas mixture at a selected temperature is quantifiable as a value, and the value of the response of that material is constant or varies by no more than about twenty percent during exposure of the material to the gas mixture at the selected temperature for period of at least about one minute.

126. An apparatus according to claim 120 wherein the component gases in the gas mixture are not separated.

127. An apparatus according to claim 120 comprising means for calculating the concentration within the gas mixture of at least one individual gas component.

128. An apparatus according to claim 120 wherein the chemo/electro-active materials comprise an array of first and second chemo/electro-active materials, each chemo/electro active material exhibiting a different electrical response characteristic, upon exposure at a selected temperature to the gas mixture, than each of the other chemo/electro-active materials, wherein the chem/electro-active materials are selected from the pairings in the group consisting of
(a) the first material is $M^1O_x$, and the second material is $M^1{}_aM^2{}_bO_x$;
(b) the first material is $M^1O_x$, and the second material is $M^1{}_aM^2{}_bM^3{}_cO_x$;
(c) the first material is $M^1{}_aM^2{}_bO_x$, and the second material is $M^1{}_aM^2{}_bM^3{}_cO_x$;
(d) the first material is a first $M^1O_x$, and the second material is a second $M^1O_x$;
(e) the first material is a first $M^1{}_aM^2{}_bO_x$, and the second material is a second $M^1{}_aM^2{}_bO_x$; and
(f) the first material is a first $M^1{}_aM^2{}_bM^3{}_cO_x$, and the second material is a second $M^1{}_aM^2{}_bM^3{}_cO_x$; wherein $M^1$ is selected from the group consisting of Ce, Co, Cu, Fe, Ga, Nb, Ni, Pr, Ru, Sn, Ti, Tm, W, Yb, Zn, and Zr;
$M^2$ and $M^3$ are each independently selected from the group consisting of Al, Ba, Bi, Ca, Cd, Ce, Co, Cr, Cu, Fe, Ga, Ge, In, K, La, Mg, Mn, Mo, Na, Nb, Ni, Pb, Pr, Rb, Ru, Sb, Sc, Si, Sn, Sr, Ta, Ti, Tm, V, W, Y, Yb, Zn, and Zr, but $M^2$ and $M^3$ are not the same $M^1{}_aM^2{}_bM^3{}_cO_x$;
a, b and c are each independently about 0.0005 to about 1; and
x is a number sufficient so that the oxygen present balances the charges of the other elements in the compound.

129. An apparatus according to claim 120 wherein the chemo/electro-active materials comprise an array of chemo/electro-active materials, each chemo/electro-active material exhibiting a different electrical response characteristic, upon exposure at a selected temperature to the gas mixture, than each of the other chemo/electro-active materials,
wherein at least one chemo/electro-active material is selected from the group consisting of $M^1O_x$, $M^1{}_aM^2{}_bO_x$; and $M^1{}_aM^2{}_bM^3{}_cO_x$;
wherein $M^1$ is selected from the group consisting of Ce, Co, Cu, Fe, Ga, Nb, Ni, Pr, Ru, Sn, Ti, Tm, W, Yb, Zn, and Zr;
$M^2$ and $M^3$ are each independently selected from the group consisting of Al, Ba, Bi, Ca, Cd, Ce, Co, Cr, Cu, Fe, Ga, Ge, In, K, La, Mg, Mn, Mo, Na, Nb, Ni, Pb, Pr, Rb, Ru, Sb, Sc, Si, Sn, Sr, Ta, Ti, Tm, V, W, Y, Yb, Zn, and Zr, but $M^2$ and $M^3$ are not the same in $M^1{}_aM^2{}_bM^3{}_cO_x$;
a, b and c are each independently about 0.0005 to about 1; and
x is a number sufficient so that the oxygen present balances the charges of the other elements in the compound.

130. An apparatus according to claim 120 wherein the gas mixture comprises one or more members of the group consisting of oxygen, carbon monoxide, a nitrogen oxide, a hydrocarbon, $CO_2$, $H_2S$, sulfur dioxide, a halogen, hydrogen, water vapor, ammonia, alcohol, a solvent vapor, an ether, a ketone, an aldehyde, a carbonyl, and a microorganism.

131. An apparatus according to claim 120 wherein the gas mixture comprises one or more members of the group consisting of oxygen, a nitrogen oxide, a hydrocarbon, and ammonia.

132. An apparatus according to claim 120 wherein the gas mixture comprises one or more members of the group consisting of a nitrogen oxide and ammonia.

133. An apparatus according to claim 120 wherein the gas mixture comprises one or more members of the group consisting of oxygen and a hydrocarbon.

134. An apparatus according to claim 120 wherein the gas mixture is an emission from a combustion process.

135. An apparatus according to claim 120 wherein the gas mixture is provided from a manufacturing process, a waste stream, environmental monitoring, or a medical, agriculture, food or beverage operation.

136. An apparatus according to claim 120 wherein the multi-component gas mixture is emitted by a process, or is a product of a chemical reaction that is transmitted to a device, and wherein the apparatus further comprises means for utilizing the electrical responses for controlling the process or the device.

* * * * *